(12) United States Patent
Maillere et al.

(10) Patent No.: US 6,649,166 B1
(45) Date of Patent: Nov. 18, 2003

(54) PEPTIDES AND PROTEINS FOR DESENSITIZING SUBJECTS ALLERGIC TO BEE VENOM AND COMPOSITIONS CONTAINING SAME

(75) Inventors: Bernard Maillere, Versailles (FR); Sandra Pouvelle, Nozay (FR); Catherine Texier, Orsay (FR); André Menez, Magny-les-Hameaux (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/890,065

(22) PCT Filed: Jan. 19, 2000

(86) PCT No.: PCT/FR00/00109

§ 371 (c)(1),
(2), (4) Date: Mar. 28, 2002

(87) PCT Pub. No.: WO00/44887

PCT Pub. Date: Aug. 3, 2000

(30) Foreign Application Priority Data

Jan. 27, 1999 (FR) .............................. 99 00879

(51) Int. Cl.[7] ........................ A61K 38/04; A61K 39/00; C07K 7/00
(52) U.S. Cl. ................ 424/185.1; 424/192.1; 424/193.1; 514/2; 514/12; 514/14; 530/327; 530/350
(58) Field of Search ................ 530/350, 327; 424/185.1, 192.1, 193.1; 514/2, 885, 14, 12

(56) References Cited

U.S. PATENT DOCUMENTS 5,552,529 A * 9/1996 Rearden

FOREIGN PATENT DOCUMENTS

WO   WO 94/04171   3/1994

OTHER PUBLICATIONS

Dierdre O'Sullivan et al., "Characterization of the Specificity of Peptide Binding To Four DR Haplotypes", *J. Immunol.*, 1990, vol. 145, No. 6, pp. 1799–1808.

Jose M. Carballido et al., "T Cell Epitope Specificity in Human Allergic and Nonallergic Subjects to Bee Venom Phospholipase A2[1]", *J. Immunol.*, 1993, vol. 150, No. 8, Pt. 1, pp. 3582–3591.

Mohan Dhillon et al., "Mapping Human T Cell Epitopes on Phospholipase $A_2$ : The Major Bee–Venom Allergen", *Journal of Allergy and Clinical Immunology*, vol. 90, vol. 1, Jul. 1992, pp. 42–51.

U. Müller et al., "Successful Immunotherapy With T–Cell Epitope Peptides of Bee Venom Phospholipase A2 Induces Specific T–Cell Anergy in Patients Allergic to Bee Venom", *Journal of Allergy and Clinical Immunology*, vol. 101, No. 6, Jun. 1998, pp. 747–754.

Catherine Texier et al., "On the Diversity and Heterogeneity of $H-2^d$–restricted determinants and T Cell Epitopes Form the Major Bee Venom Allergen", *Int. Immunol*, vol. 11, No. 8, Aug. 1999, pp. 1313–1325.

Alexander Faith et al., "An Altered Peptide Ligand Specifically Inhibits Th2 Cytokine Synthesis by Abrogating TCR Signaling", *J. Immunol.*, vol. 162, No. 3, Feb. 1, 1999, pp. 1836–1842.

* cited by examiner

*Primary Examiner*—Christina Chan
*Assistant Examiner*—Marianne DiBrino
(74) *Attorney, Agent, or Firm*—Morgan Lewis & Bockius LLP

(57) ABSTRACT

The invention concerns peptides and proteins for desensitizing specifically the vast majority of subjects allergic to bee venom and compositions containing said peptides or proteins. The peptides are selected in the group consisting of: the fragment (1) corresponding to positions P85-97 of the major bee venom allergen, the fragment (2) corresponding to positions P81-93 of the major bee venom allergen, the fragment (3) corresponding to positions P94-106 of the major bee venom allergen, the fragment (4) corresponding to positions P76-88 of the major bee venom allergen, the fragment (5) corresponding to positions P77-94 of the major bee venom allergen, and the fragment (6) corresponding to positions P122-134 of the major bee venom allergen, fragments (I) and (2) forming group (1); fragment (3) forming group (II); fragments (4) and (4) forming group (III) and fragment (6) forming group IV and the mutated fragments of said fragments (1) to (6) which have a binding activity with MHC class (II) molecules identical or higher than those of said fragments (1) to (6). The invention also concerns compositions containing said peptides or proteins.

13 Claims, 8 Drawing Sheets

Figure 2:
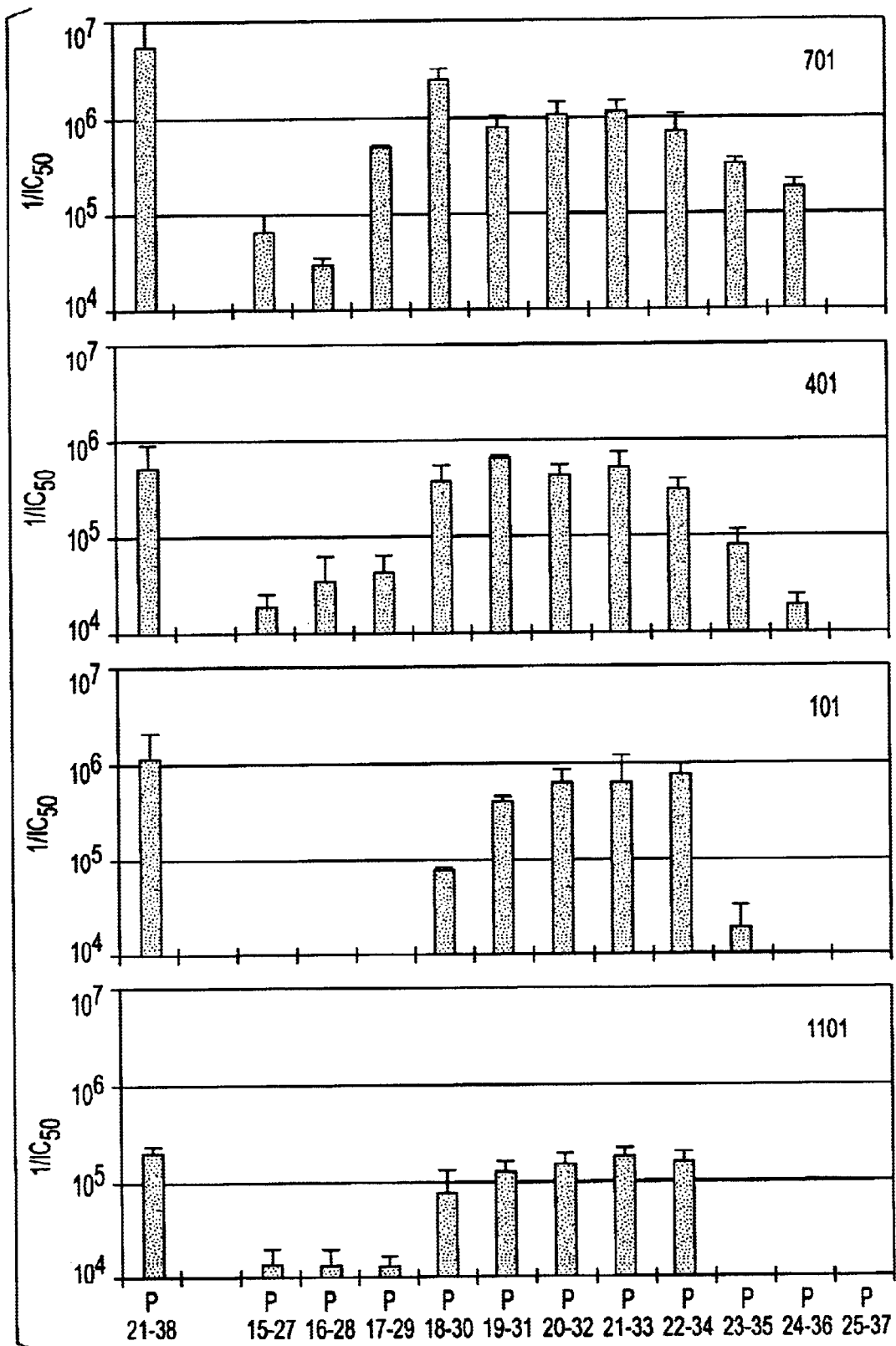

| | | | | | | | | | |
|---|---|---|---|---|---|---|---|---|---|
| 1 | 2 | 3 | 4 | 5 | 6 | 7 | 8 | 9 | 10 |
| I | I | Y | P | G | T | L | W | C | G |
| 11 | 12 | 13 | 14 | 15 | 16 | 17 | 18 | 19 | 20 |
| H | G | N | K | S | S | G | P | N | E |
| 21 | 22 | 23 | 24 | 25 | 26 | 27 | 28 | 29 | 30 |
| L | G | R | F | K | H | T | D | A | C |
| 31 | 32 | 33 | 34 | 35 | 36 | 37 | 38 | 39 | 40 |
| C | R | T | H | D | M | C | P | D | V |
| 41 | 42 | 43 | 44 | 45 | 46 | 47 | 48 | 49 | 50 |
| M | S | A | G | E | S | K | H | G | L |
| 51 | 52 | 53 | 54 | 55 | 56 | 57 | 58 | 59 | 60 |
| T | N | T | A | S | H | T | R | L | S |
| 61 | 62 | 63 | 64 | 65 | 66 | 67 | 68 | 69 | 70 |
| C | D | C | D | D | K | F | Y | D | C |
| 71 | 72 | 73 | 74 | 75 | 76 | 77 | 78 | 79 | 80 |
| L | K | N | S | A | D | T | I | S | S |
| 81 | 82 | 83 | 84 | 85 | 86 | 87 | 88 | 89 | 90 |
| Y | F | V | G | K | M | Y | F | N | L |
| 91 | 92 | 93 | 94 | 95 | 96 | 97 | 98 | 99 | 100 |
| I | D | T | K | C | Y | K | L | E | H |
| 101 | 102 | 103 | 104 | 105 | 106 | 107 | 108 | 109 | 110 |
| P | V | T | G | C | G | E | R | T | E |
| 111 | 112 | 113 | 114 | 115 | 116 | 117 | 118 | 119 | 120 |
| G | R | C | L | H | Y | T | V | D | K |
| 121 | 122 | 123 | 124 | 125 | 126 | 127 | 128 | 129 | 130 |
| S | K | P | K | V | Y | Q | W | F | D |
| 131 | 132 | 133 | 134 | | | | | | |
| L | R | K | Y | | | | | | |

*FIG. 1*

FIG. 7

PEPTIDES AND PROTEINS FOR DESENSITIZING SUBJECTS ALLERGIC TO BEE VENOM AND COMPOSITIONS CONTAINING SAME

The present invention relates to peptides and proteins capable of desensitizing, in a specific manner, the great majority of subjects allergic to bee venom, and to compositions containing said peptides or proteins.

Immediate allergy to Hymenoptera (bee, wasp, hornet) affects 15 to 20% of the population, if prick tests are taken into account, but only 0.1 to 0.5% of the population is exposed to an anaphylactic-type accident (1, 2). This allergy is characterized by varying manifestations ranging from local swelling to systemic reactions such as urticaria, angioedema or anaphylactic shock. Given the suddenness of the stings, desensitization (specific immunotherapy or SIT) with venoms constitutes the preferred treatment for this allergy but is not without danger. Indeed, 13% of patients desensitized with bee venom and 5% in the case of wasp venom are victims of side effects (3). The search for a better tolerated and equally effective SIT is therefore necessary, in particular for bee venom.

The speed of the reactions observed in patients allergic to bee venom is characteristic of an immediate-type allergy which is mediated by IgEs specific for the constituents of the venom. The complex mechanism of these reactions is summarized below.

IgEs appear gradually under the repeated action of stings and before any symptom becomes apparent. Although the bee venom comprises numerous peptides and proteins, all the components do not appear to be allergenic (4). Melittin, for example, induces IgEs in only 30% of patients, whereas the proportion increases to more than 90% for phospholipase A2 (PLA2) which is, as a result, considered to be the major allergen (API m1). The protein sequence of bee venom phospholipase A2 (API m1) is illustrated in FIG. 1 (SEQ ID NO: 8); this sequence is deduced from that of the complementary cDNA (36).

IgEs possess the property of binding, via their Fc fragment, to receptors situated on the tissue mastocytes and the blood basophils. When the allergen forms a complex with the specific IgEs bound to the membrane of the basophils or mastocytes, it causes degranulation of the cells and the release of molecules which are responsible for the principal manifestations observed during an allergic accident. IgEs are not solely responsible for the allergy because although the IgE level is an indicator for the disease, it has no diagnostic value for the state of the patients. It is not rare for patients to have high IgE levels without showing symptoms. The appearance of IgEs in allergic patients results from the production of type TH2 cytokines such as IL-4, IL-5 and IL-13 and is inhibited by the synthesis of IFN-γ (6).

It is mainly the CD4$^+$ T lymphocytes which produce these cytokines. Specific T cells which secrete more IL-4 than IFN-γ are effectively found in allergic patients, whereas the T cells isolated from nonallergic subjects produce more IFN-γ than IL-4.

The TH2-type CD4$^+$ T lymphocytes specific for the venom components therefore actively participate in the appearance and the maintenance of the allergy.

To protect the subjects allergic to bee venom, it was proposed long ago to desensitize the allergic subjects by specific immunotherapy (or SIT). The immunological mechanisms of SIT which are responsible for the improvement in the patient's condition remain poorly understood. The induction of specific IgGs and of an IgG4 subclass (7) as well as the generation of suppressive CD8$^+$ T cells (8) were initially proposed to account for the efficacy of the treatment. However, it was more recently observed that during the desensitization to bee venom, the proliferation of the CD4$^+$ T lymphocytes specific for the allergen decreases while the secretion of IL-4 and IL-5 decreases (9, 10) or is diverted toward the production of IFN-γ (11). Very similar results were also obtained with pollen allergens (12). These observations appear to indicate that the improvement in the patient's condition results from a peripheral tolerance or from a drift toward a TH1-type profile for the CD4$^+$ T lymphocytes specific for the allergen. They are furthermore in agreement with experiments carried out in animals. It has indeed been shown for several antigens that under injection conditions similar to those used to desensitize (such as subcutaneous injection) the anergy of the T lymphocytes is induced while a high response is observed for the same antigens when they are injected in the presence of adjuvant (13, 14). All these experiments make it possible to consider the CD4$^+$ T lymphocytes specific for bee venom as the target cells for immunotherapy.

The CD4$^+$ T lymphocytes possess a rearranged T receptor which allows them to selectively recognize peptide fragments derived from the degradation of the antigen by the presenting cells and presented by the Major Histocompatibility Complex class II (MHC II) molecules (15). The determinants which these peptide fragments carry and which the T lymphocytes effectively recognize are called T epitopes.

During desensitization, it is these determinants which are recognized by the T lymphocytes and which therefore constitute the basic elements for the production of alternative molecules for specific immunotherapy.

It has indeed been observed in vivo in mice for the allergens Fel d1 (cat hair), Der p1 (acarian: *Dermatophagoides pterissimus*) and Bet v1 (birch pollen) that the nasal, oral or subcutaneous administration of peptides carrying T epitopes of these allergens inhibits the activation of the specific T lymphocytes (16–18) and modulates the allergic reaction (16, 18).

Ideally, the desensitizing molecules should possess all the epitopes of the allergen and be free of reactivity toward the IgEs, so as to avoid the risks of accidents.

Several types of molecule are already being studied, including in the context of bee venom allergy and consist either of peptide fragments or of modified proteins.

Peptide Fragments

Using an empirical approach, the use of peptide fragments (19) to desensitize allergic patients has been proposed on several occasions as an alternative to conventional specific desensitization, including for bee venom allergy (20, 21).

These fragments generally no longer possess reactivity toward IgEs, but they may also have lost their capacity to be recognized by T lymphocytes.

More recently, allergen peptide fragments were chosen on the basis of their capacity to stimulate T lymphocytes in allergic patients (22).

In the case of the major bee venom allergen (API m1), fragments 50–69 and 83–97 have been described as being active during a study comprising a single patient (23).

In a study comprising forty patients (24), it is fragments 45–62 and 81–92 and 113–124 which proved to be active. These three fragments are only T epitopes for 25 to 45% of the patients and the authors do not exclude the existence of other epitopes (24, 25). These three peptides are undergoing clinical trial and appear to give encouraging results (22). Muller et al. (22) have used them to desensitize five allergic patients whose T lymphocytes proliferate in the presence of these peptides. No serious systemic effect was observed and the patients became tolerant to bee stings. This demonstrates the benefit of using peptides for desensitizing, but does not make it possible to extend the use of these peptides to other patients.

Another trial using peptides was set up for the cat allergen (Fel d1) (26). Several applications relating to peptides from ragweed (WO 93/21321; WO 96/13589), from Japanese cedar pollen (WO 93/01213; WO 94/01560) and from ryegrass pollen (WO 94/21675; WO 94/16068) have been filed.

All the peptides described in these applications were chosen on the basis of the stimulation of T lymphocytes in a group of allergic patients.

The approach followed by these various authors (23, 24 and 30) is based on cellular tests and not on binding tests. The results observed show that the active peptides vary according to the patients. In the latter three studies, the peptides containing the zone 80–90 are those which are most often a T epitope. They also show that the lymphocytes of several patients are stimulated by peptides containing the C-terminal portion of API m1.

For example, Kämmerer et al. (30) propose, according to the same principle of the stimulation test, using long fragments of API m1, in particular fragment 90–134. However, these fragments are specific for certain patients and are not suitable for a significant set of patients because their selection does not take into account the HLA type of the patients.

The stimulation tests indeed make it possible to select peptides suitable for desensitizing a given patient (22), but do not make it possible to extend the use of these peptides to patients other than those for which they were produced.

Modified Proteins

Another alternative to the use of native allergens is that of allergens modified such that they no longer exhibit reactivity toward the IgEs specific for the allergen, while preserving their reactivity toward the T lymphocytes. As the IgEs are mainly directed against conformational epitopes, the loss of reactivity can be easily obtained by destroying the three-dimensional structure of the allergen, which does not modify by the T epitopes. That is what was done for mutants of Der f2 (27) and Der p2 (28) in which the disulfide bridges were broken. Another way of proceeding is to introduce into the allergen point mutations which affect the recognition of the IgEs without modifying the three-dimensional structure (29). The small number of mutations introduced is thought not to modify the T epitopes.

The large differences observed between studies indicate the interindividual variability of the T epitopes and obviously make the choice of desensitizing molecules difficult. Furthermore, these studies, which use only a group of allergic patients, do not make it possible to ensure that all the T epitopes are conserved in the desensitizing molecule.

Accordingly, the inventors set themselves the objective of providing a set of peptides capable of desensitizing the great majority of subjects allergic to bee venom. Such a set of peptides has the property of being effective in a large number of subjects, whereas the prior art peptides are active in one allergic subject but may be completely ineffective for another subject because the latter does not recognize the allergen by the same determinants.

To do this, the inventors have defined a relationship between the peptide sequences of the major bee venom allergen (API m1) and MHC class II molecules, both in the alleles of the HLA-DRB1 gene (1st gene), and the alleles of the DRB3, DRB4 and DRB5 genes (2nd gene), which are predominant in Caucasian populations. This relationship makes it possible, unexpectedly, to define molecules for desensitization and for preventive treatment of allergy to bee venom which takes into account the polymorphism of the MHC class II, in particular HLA-DR molecules, and which by virtue of their high specificity, induce better desensitization which results in a significantly reduced risk of accidents (shocks) during desensitization. This represents an additional advantage for the preventive use of such peptides.

The molecules of the major histocompatibility complex (MHC) class II (HLA II in man) are heterodimers expressed on presenting cells and present the T epitopes of the antigens to the $CD4^+$ T lymphocytes. These molecules are capable of binding a large repertoire of peptides having very different sequences, which allows them to present several peptides per antigen to the T cells.

There are four different types of MHC II molecules per individual (2 HLA-DR, 1 HLA-DQ and 1 HLA-DP). The HLA-DR molecule, whose β chain is encoded by the DRB1 gene (1st gene) is the most highly expressed. There have currently been recorded more than 200 different alleles for DRB1, which define various antigens or types, as summarized in Table 1 below.

TABLE I

Molecules expressed by various HLA-DRB1 alleles

| Antigen | Allele | Alias |
|---|---|---|
| DR1 | DRB1*0101 | DR1 |
| DR2 | DRB1*1501 | DR2w2b |
| DR3 | DRB1*0301 | DR3w17 |
| DR4 | DRB1*0401 | DR4w4 |
|  | DRB1*0405 | DR4w15 |
| DR7 | DRB1*0701 | DR7 |
| DR8 | DRB1*0802 | DR8w2 |
| DR9 | DRB1*0901 | DR9 |
| DR11 | DRB1*1101 | DR5w11 |
| DR12 | DRB1*1201 | DR5w12 |
| DR13 | DRB1*1301 |  |
|  | DRB1*1302 | DR6w19 |

Each allele possesses its own binding properties. It therefore binds a repertoire of peptides specific to it and which differs from that for another allele, even on the same antigen. The broad specificity of the HLA II molecules and the existence of several isoforms and of a high polymorphism mean that many different fragments of the antigen can be presented to the T lymphocytes.

The frequencies of each allele (1st gene) are not identical and vary from one population to another (35):

the DRB1*1304 allele represents, on its own, 25.4% of the alleles in the Senegalese population against 0% in Germany and in Japan, the DRB1*0301 allele is observed with a frequency of 10% in the Senegalese and the Germans but only at 0.4% in the Japanese, in France, only seven alleles exceed 5%. They are the alleles DRB1*0101, DRB1*0301, DRB1*0401, DRB1*0701, DRB1*1101, DRB1*1301 and DRB*1501, as illustrated in Table II below.

TABLE II

Frequency of the HLA-DR alleles
in several Caucasian populations

|          | FRA  | DAN  | GER  | ITA  | ROU  | SPA  | US   | CAN  |
|----------|------|------|------|------|------|------|------|------|
| DRB1*0101 | 9.3  | 13.0 | 6.7  | 6.5  | 7.6  | 6.6  | 7.3  | 5.6  |
| DRB1*0301 | 10.9 | 10.2 | 9.4  | 10.5 | 11.4 | 6.7  | 9.5  | 12.3 |
| DRB1*0401 | 5.6  | 17.6 | 8.1  | 2.3  | 4.2  | 5.6  | 6.7  | 9.5  |
| DRB1*0701 | 14.0 | 14.8 | 12.3 | 12.5 | 8.3  | 18.9 | 14.4 | 9.4  |
| DRB1*1101 | 9.2  | 0.9  | 9.2  | 12.4 | 7.3  | 1.0  | 4.4  | 2.6  |
| DRB1*1301 | 6.0  | 8.3  | 4.5  | 4.8  | 4.4  | 4.5  | 5.1  | 4.7  |
| DRB1*1501 | 8.0  | 17.6 | 7.8  | 5.6  | 6.2  | 9.4  | 10.3 | 10.4 |
| Total    | 63   | 82   | 58   | 55   | 49   | 53   | 58   | 55   |

They represent, on their own, 63% of the French population. These same alleles are also the most abundant in the other Caucasian populations. Their frequencies vary from 53% (in Spain) to 82% (in Denmark). For the United States and Canada, they represent 58 and 55% of the population, respectively. They therefore represent, on their own, 53 to 82% of the alleles in Caucasian populations and are part of the various specificities of HLA-DR series.

Figure 5:
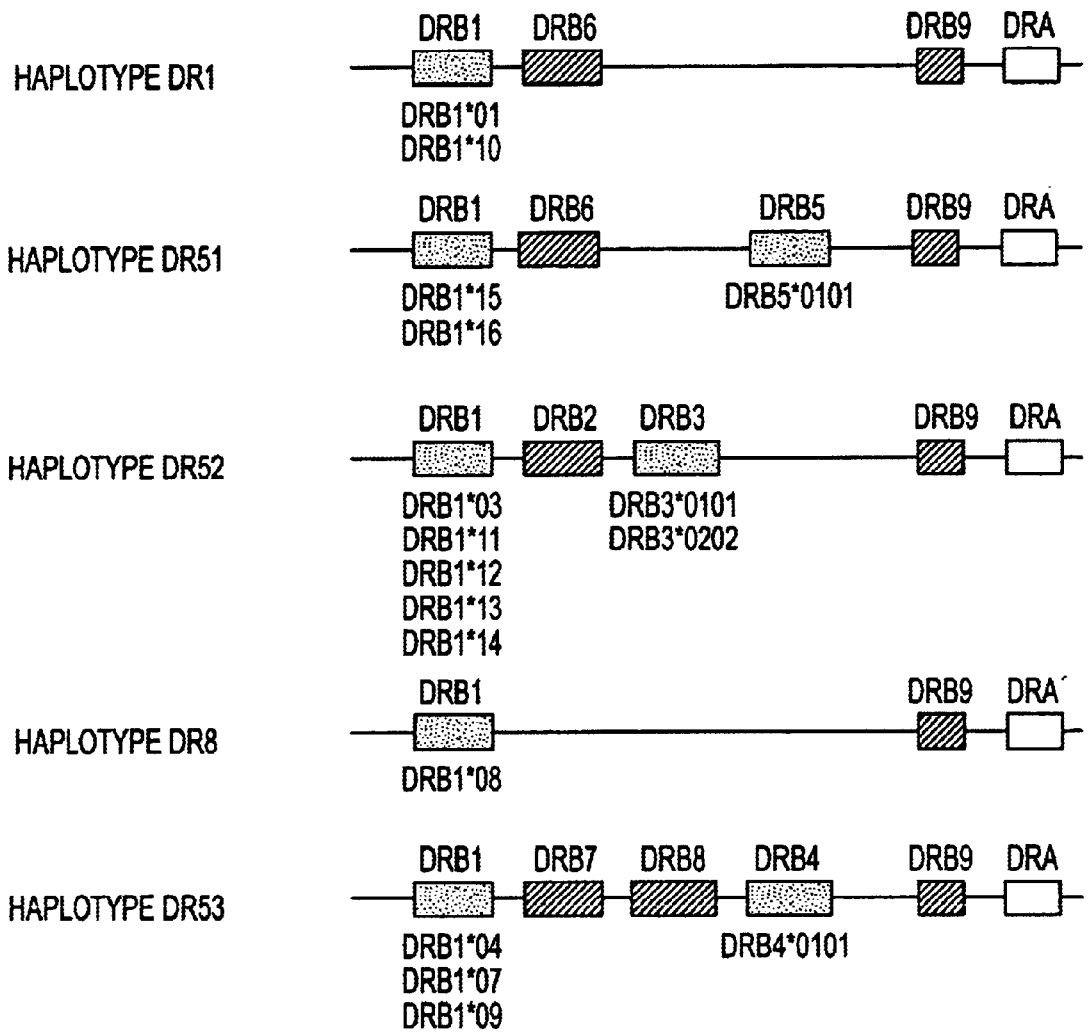

The 2nd gene encodes the HLA-DRB3, -DRB4 and -DRB5 molecules which are HLA-DR molecules whose β chain is not encoded by the DRB1 gene. Although less well known than the molecules derived from the 1st gene, these HLA molecules are functional and are capable of presenting peptides to the T lymphocytes (56–59). Their main advantage for the immunotherapy is that alleles such as DRB3*0101 (9.2%), DRB4*0101 (28.4%) and DRB5*0101 (7.9%) are very frequent in the Caucasian population. They cover, on their own, 45% of the gene frequency. They are systematically associated with another HLA-DR molecule and can therefore complement its specificity. A strong binding disequilibrium exists between the 1st and 2nd gene, that is to say that a 2nd gene is very often associated with particular alleles of the 1st gene. The set of DR pseudogene and genes present on the same chromosome constitutes a DR haplotype (FIG. 5). Each haplotype is defined by the second DR molecule which characterizes it.

The role of the MHC II molecules in allergy was historically initiated by the discovery of the association between the level of IgE against a given allergen and certain alleles. These associations concern numerous allergens of low molecular mass such as Amb a5, Lol p3 and Amb a6 (31) which are allergens for which the relative risks are the greatest. These associations are not systematic or correspond to very low relative risks.

In the case of bee venom, it has been shown that the HLA-DR7 allele is more frequent in allergic patients than in the control population (32) whereas the HLA-DR4 allele is by contrast underrepresented in those allergic to bee venom (33).

The control of the IgE (and IgG) response by the class II molecules is even clearer in mice (34). The H-$2^d$ and H-$2^k$ mice are indeed good responders whereas the H-$2^b$ mice respond little or not at all to this allergen.

The subject of the present invention is peptides capable of desensitizing a subject allergic to bee venom, characterized in that they are selected from the group consisting of:
  fragment (1) corresponding to positions P85-97 of the major bee venom allergen,
  fragment (2) corresponding to positions P81-93 of the major bee venom allergen,
  fragment (3) corresponding to positions P94-106 of the major bee venom allergen,
  fragment (4) corresponding to positions P76-88 of the major bee venom allergen,
  fragment (5) corresponding to positions P77-94 of the major bee venom allergen,
  fragment (6) corresponding to positions P122-134 of the major bee venom allergen, and
  the mutated fragments of said fragments (1) to (6) which exhibit an MHC class II molecule binding activity identical to or higher than those of said fragments (1) to (6).

Fragments (1) and (2) form group I; fragment (3) forms group II; fragments (4) and (5) form group III and fragment (6) forms group IV.

Such peptides comprise T epitopes or determinants which interact with one or more HLA-DR molecules derived from the DRB1 genes or other DRBs (DRB3, DRB4 and DRB5).

The present invention also includes the peptides as defined above, polymerized.

The site for binding of the peptides to the class II molecules is situated between the α helices of the α1 and α2 domains and forms a groove which is open at both ends. This opening allows the binding of peptides with varying sizes, in general from 13 to 25 amino acids. The anchoring of the peptides to the MHC II molecules occurs by means of hydrogen bonds between the backbone of the peptide and the amino acids of the groove and by means of residues accommodated by pockets for specificity. Five pockets, called P1, P4, P6, P7 and P9, correspond to the amino acid of the peptide which it accommodates, the first position being that which is in the first pocket, receive amino acids of the peptide and are composed of conserved or polymorphic residues. The polymorphic residues are responsible for various specificities between MHC II molecules. Since the binding site is open, two peptides binding one MHC II molecule may do so according to different modes, that is to say using different anchoring residues in their sequence.

Peptides P81-93 and P85-97, mutated in at least one residue, correspond to one of the pockets P1, P4, P6, P7 and P9 are in particular included in the invention.

In order to be able to introduce residues which preserve or increase the binding activity, the modes of interaction of the peptides P81-93 and P85-97 with respect to the HLA-DR molecules capable of binding them were studied. The approach chosen was to introduce into each position an alanine so as to evaluate the role of the side chain in the interaction or a lysine which is a basic and bulky amino acid. If necessary, a combination of mutations was introduced. By way of example, a reduction in activity caused by substitutions of phenylalanine 88 by a lysine or an alanine is observed in FIG. 6. Other reductions in activity are observed a positions situated at 3, 5 and 8 amino acids from phenylalanine 88. This activity profile corresponds to a mode of binding where positions F88, I91 T93 and Y96 are accommodated by the pockets P1, P4, P6 and P9, respectively, of the molecules HLA-DRB3*0101, HLA-DRB5*0101, HLA-DRB1*1301 and HLA-DRB1*0701. This mode of association was confirmed by molecular modeling for the complexes: P85-97/DRB3*0101, P85-97/DRB5*0101 and P81-93/DRB4*0101. All the results are given in FIG. 7. It is observed that on sequence 81–97, there are at least six modes of binding to the HLA-DR molecules. It is also observed that mode I is common to eight molecules whereas modes V and VI are specific to a single molecule.

The fact that it is possible to know exactly how the peptide is positioned on each HLA-DR molecule makes it possible to propose sequence modifications:
  at positions P1, P4, P6, P7 and P9, it is possible to introduce modifications which are compatible with the known specificities of the HLA molecules (61). It is for example probable that tyrosine 87 can be changed by a phenylalanine without any loss of activity. On the other hand, the substitution of phenylalanine 88 by a tyrosine should not cause a loss of activity for, for example, the molecules DRB1*0101 and DRB1*0401 but should reduce the activity of the peptide for molecules such as DRB1*0301 or DRB3*0101.

it is also possible to increase the affinity of the peptide by modifying, in an optimum manner, residues P1, P4, P6, P7 and P9. This is what was done for residues 89 and 84. Residue 89 can be advantageously modified to leucine or to threonine (Table IX). In particular, the substitution by leucine increases the affinity of the peptide 85–97 by a factor of 10 and 12 for the molecules DRB3*0101 and DRB1*0301, respectively. In the case of DRB1*0301, this increase is explained by the fact that asparagine N89 at position P1 is not optimum for this molecule, unlike leucine (61). Likewise, the substitution of glycine 84 by an alanine increases the affinity by a factor of 5 for DRB1*1501. This increase is in agreement with the positioning of glycine 84 in P1 and ought to be even higher if a hydrophobic residue such as leucine or isoleucine is introduced. On the other hand, the substitution of aspartic acid D92 systematically reduces the affinity for DRB1*0301. This reduction in activity is in accordance with the anchoring role of aspartic acid in P4 for this molecule.

at positions P-2, P-1, P2, P3, P5, P8, P10 and P11, modifications may be introduced without fear of causing major losses in affinity.

TABLE IX

Relative activities of the modified peptides relative to the peptide P85–97A

| | Peptides | | | | |
|---|---|---|---|---|---|
| | N89L | N89T | D92N | D92L | D92T |
| DRB1*0101 | 2 | 1 | 2 | 1 | 2 |
| DRB1*0301 | 12 | 7 | −57 | −29 | −12 |
| DRB1*0401 | 4 | 2 | 3 | −2 | 4 |
| DRB1*0701 | 4 | 3 | 3 | 12 | 9 |
| DRB1*1101 | 8 | 2 | 8 | 7 | 13 |
| DRB1*1301 | 1 | 1 | 1 | 2 | 1 |
| DRB3*0101 | 10 | 2 | 1 | 2 | 2 |
| DRB5*0101 | 1 | −1 | 2 | 2 | 2 |

The peptides N89L, N89T, D92N, D92L, D92T are analogs of the peptide P85-97A. The first letter corresponds to the initial amino acid, the number to its position in the Api m1 sequence and the second letter to the modification introduced. The data correspond to the ratios between the $IC_{50}$ values for the analogs and that for the reference peptide P85-97A. A—sign means a loss of activity and the absence of a sign means an increase in activity.

The peptide P85-97A possesses an alanine at position 95 as a replacement for cysteine. This substitution does not cause any modification in activity regardless of the HLA-DR molecule.

In accordance with the invention, at least one of positions P1, P4, P6 and P9 of the fragments (1), with reference to FIG. 7 is mutated.

According to an advantageous feature of this embodiment, said fragments (1) comprise one of the following mutated amino acids: N89L, N89T, C95A, G84L, G84I.

Also in accordance with the invention, at least one of the positions P-2, P-1, P2, P3, P5, P8, P10 and P11 of the fragments (1), with reference to FIG. 7, is mutated.

The subject of the present invention is also desensitizing compositions for bee venom allergies, characterized in that they comprise:

at least one peptide selected from group A consisting of:
- the peptides of group I, as defined above, and
- the peptides consisting of fragments of at least 13 amino acids which are included in or comprise the fragment corresponding to positions P81-97 of the major bee venom allergen (API m1) and which bind at least to the HLA-DR molecules encoded by the HLA alleles DRB1*0101, DRB1*0301, DRB1*0401, DRB1*0701, DRB1*1101, DRB1*1301 and DRB1*1501 (molecules DR1, DR3, DR4, DR7, DR11, DR13 and DR2), with a binding activity <1000 nM, and at least one pharmaceutically acceptable vehicle.

Such compositions which are particularly suitable for the patient may be advantageously used preventively or curatively.

According to an advantageous embodiment of said compositions, they preferably consist of a mixture of peptides comprising:

at least one group A peptide as defined above and at least one other peptide selected from the following groups:

the peptides selected from group B consisting of:
- the peptides of group II, as defined above, and
- the peptides consisting of fragments of at least 13 amino acids which are included in or comprise the fragment corresponding to positions 94–106 of the major bee venom allergen (API m1) and which bind at least to the HLA-DR molecules expressed by the alleles DRB1*0101, DRB1*0401 and DRB1*1101 (molecules DR1, DR4 and DR11), with a binding activity <1000 nM, the peptides selected from group C consisting of:
- the peptides of group III, as defined above, and
- the peptides consisting of fragments of at least 13 amino acids which are included in or comprise the fragment corresponding to positions P76-94 of the major bee venom allergen and which bind at least to the HLA-DR molecules expressed by the alleles DRB1*0701, DRB1*1101 and DRB1*1501 (molecules DR7, DR11 and DR2), with a binding activity <1000 nM, and the peptides selected from group D consisting of:
- the peptides of group IV, as defined above, and
- the peptides consisting of fragments of at least 13 amino acids which are included in or comprise the fragment corresponding to positions P122-134 of the major bee venom allergen and which bind at least to the HLA-DR molecules expressed by the alleles DRB1*1101, DRB1*1301 and DRB1*1501 (molecules DR11, DR13 and DR2), with a binding activity <1000 nM.

According to another embodiment of said compositions, they comprise, in addition, optionally the peptide corresponding to positions P18-30 and/or the peptide corresponding to positions P45-62 and/or the peptide corresponding to positions P57-74 and/or the peptide corresponding to positions P65-82 and/or the peptide corresponding to positions P111-123, of the major bee venom allergen, in accordance with Tables IIIa and IIIb below and/or the peptides including the abovementioned peptides.

TABLE IIIa

Peptides representative of the various zones of interaction between the major bee venom allergen and the HLA-DR molecules (1st gene) encoded by the DRB1 gene

| 101 | 401 | 1101 | 701 | 301 | 1301 | 1501 |
|---|---|---|---|---|---|---|
|  |  |  | P18–30 |  |  |  |
|  |  |  | P45–62 |  |  |  |
|  |  |  |  | P57–74 |  |  |
|  |  |  |  |  |  | P65–82 |
|  |  |  |  |  |  | P76–88 |
|  | P77–94 | P77–94 |  |  |  |  |
|  |  |  |  |  |  | P81–93 |
| P85–97 | P85–97 | P85–97 | P85–97 | P85–97 | P85–97 |  |
| P94–106 | P94–106 | P94–106 |  |  |  |  |
|  |  | P111–123 |  |  |  |  |
|  |  | P122–134 |  |  | P122–134 | P122–134 |

TABLE IIIb

Peptides representative of the various zones of interaction between the major bee venom allergen and the HLA-DR molecules (2nd gene) in which the β chain is not encoded by the DRB1 gene

| HLA-DR alleles (2nd gene) | | | Cumulative |
|---|---|---|---|
| B5*0101 | B4*0101 | B3*0101 | frequency[a] |
| 21–38 |  |  | 7.9 |
| 45–62 |  |  | 7.9 |
|  |  | 53–70 | 9.2 |
| 77–94 |  | 77–94 | 17.1 |
|  | 81–93 |  | 28.4 |
| 85–97 |  | 85–97[a] | 17.1 |
|  | 89–101 |  | 28.4 |
| 94–106 |  |  | 7.9 |
| 111–123 | 111–123 | 111–123 | 45.5 |
| 122–134 | 122–134 | 122–134 | 45.5 |

These peptides are representative of the zones of interaction with the 2nd HLA-DR molecules. They are part of the most active peptides for a given zone and are as short as possible.

[a]: the cumulative frequencies between the alleles of various genes only make sense because the 2nd molecules behave, within the Caucasian population, like an identical allelic series.

Advantageously, in said compositions:

the group I peptides may be advantageously concatenated to form a single peptide (P81-97) and/or the group III peptides may be advantageously concatenated to form a single peptide (P76-94) corresponding to positions P81-97 of the major bee venom allergen and/or the group II and group III peptides may be advantageously concatenated to form a single peptide (P76-106) corresponding to positions P81-97 of the major bee venom allergen.

In general, the compositions according to the invention comprise at least one peptide including at least one of those described in Table III and which are suitable for the patient to be desensitized.

These desensitizing compositions are defined from the activities for binding to the HLA-DR molecules of the peptides which they comprise, from the frequency of alleles toward which they are active and from the complementarity of the zones for interaction or epitopes which said peptides carry.

For a patient for whom the HLA-DR molecules which they are carrying are not known, a composition according to the invention will be preferably used which comprises at least one group A peptide.

There may be added thereto, advantageously and in order to increase the number of epitopes: a group B peptide; a group C peptide; a peptide corresponding to the concatenation of a group B peptide and of a group C peptide and/or a group D peptide.

For the patients for whom the HLA molecules are known, there will be used either the peptide defined above, or a combination of peptides including at least those described in Tables IIIa and IIIb, which correspond to the alleles which the patient possesses.

The peptides included in said compositions were advantageously selected using an HLA-DR/peptide binding test comprising (i) incubating the purified HLA-DR molecules selected from those relating to more than 5% of a given population and in particular the HLA molecules DR1, DR3, DR4, DR7, DR11, DR13 and DR2, simultaneously with various concentrations of fragments of 13 to 18 amino acids which overlap and which completely cover the API m1 sequence and with a reagent R1 consisting of a peptide fragment combined with a nonradioactive marker, such as biotin and whose sequence is different from said peptides and is chosen such that it exhibits affinity toward the chosen HLA-DR molecule, such that it can be used at a concentration <200 nM, (ii) transferring the complexes obtained on an ELISA-type plate, previously sensitized with an antibody specific for all the HLA-DR molecules, (iii) revealing the HLA-DR molecules/R1 reagent complexes, attached to the bottom of the plate by means of suitable conjugates, such as streptavidin-phosphatase and a fluorescent substrate, (iv) selecting the peptides comprising different epitopes, that is to say the most representative of the various zones of interaction between the major bee venom allergen and the HLA-DR molecules and (v) choosing the most suitable peptides as a function of the frequency of the alleles toward which they exhibit a binding activity <1000 nM, corresponding to the concentration of this peptide which inhibits 50% of the binding of the reagent R1 ($IC_{50}$).

These tests make it possible, unambiguously, to combine with each allele of the 1st gene or of the 2nd gene, the sequences of the fragments capable of binding thereto or on the contrary which do not bind thereto.

This approach makes it possible to define desensitizing compositions including peptides which bind to the largest number of different HLA-DR molecules and which can thus be advantageously desensitized for the majority of patients, even if their HLA molecules are not known.

This approach has, in addition, the advantage of allowing the selection of peptides which are significantly more specific with respect to most of the allergic subjects than the approaches seeking to select peptides on the basis of their capacity to stimulate T lymphocytes of allergic subjects.

Thus, the inventors have found that only some peptides have a binding activity with respect to several of the most frequent alleles in the Caucasian population in accordance with Tables IIIa and IIIb.

The subject of the present invention is also desensitizing compositions for bee venom allergies, characterized in that they comprise at least one modified bee venom phospholipase A2, in which the zones comprising the peptides as defined above are conserved and the zones outside the abovementioned zones are modified, such that they no longer exhibit reactivity toward the IgEs and at least one pharmaceutically acceptable vehicle.

Said zones are in particular modified by point mutation or deletion. Bee venom PLA2 is indeed capable of receiving numerous mutations and deletions (53, 54). It is therefore possible to obtain mutants no longer exhibiting reactivity toward IgEs, such as those obtained for Bet VI (55). For example, the bee PLA2 mutant in which the lysine at position 25 has been substituted is a lot less antigenic for apiarist sera than the native molecule (55).

The subject of the present invention is also the use of a modified bee venom phospholipase A2 in which the zones comprising the peptides as defined above are conserved and the zones outside the abovementioned zones are modified, such that they no longer exhibit reactivity toward the IgEs, for the preparation of a desensitizing composition for bee venom allergies.

The peptides which can be included in a desensitizing composition for bee venom allergies may be advantageously selected by a method which comprises:

(i) incubating the purified HLA-DR molecules selected from those relating either to less than 5% of a given population, that is to say those consisting of HLA-DRs other than the HLA molecules DR1, DR3, DR4, DR7, DR11, DR13 and DR2, or HLA-DR molecules from a given patient, simultaneously with various concentrations of fragments of 13 to 18 amino acids which overlap and which completely cover the API m1 sequence and with a reagent R1 consisting of a peptide fragment combined with a nonradioactive marker such as biotin and whose sequence is different from the peptides, as defined above (groups A to D) and is chosen so that it exhibits affinity toward the chosen HLA-DR molecule, such that it can be used at a concentration <200 nM, (ii) transferring the complexes obtained on a microtiter plate, previously sensitized with an antibody specific for all the HLA-DR molcules, (iii) revealing the HLA-DR molecules/R1 reagent complexes, attached to the bottom of the plate by means of suitable conjugates, such as streptavidin-phosphatase and a fluorescent substrate, (iv) selecting the peptides comprising different epitopes, that is to say the most representative of the various zones of interaction between the major bee venom allergen and the HLA-DR molecules studied and (v) choosing the most suitable peptides as a function of the frequency of the alleles toward which they exhibit a binding activity <1000 nM, corresponding to the concentration of this peptide which inhibits 50% of the binding of the reagent R1 ($IC_{50}$).

The incubation conditions are specific to each HLA-DR molecule (incubation time, pH, reagent R1, HLA-DR or peptide concentration).

The reagent R1 is selected from the group consisting of the following sequences:

PKYVKQNTLKLAT (SEQ ID NO: 1), specific for the alleles DRB1*0101, DRB1*0401, DRB1*1101,
EAEQLRAYLDGTGVE (SEQ ID NO: 2), specific for the allele DRB1*1501,
AKTIAYDEEARGLE (SEQ ID NO: 3), specific for the allele DRB1*0301,
AAYAAAKAAALAA (SEQ ID NO: 4), specific for the allele DRB1*0701,
TERVRLVTRHIYNREE (SEQ ID NO: 5), specific for the allele DRB1*1301,
ESWGAVWRIDTPDKLTGPFT (SEQ ID NO: 6), specific for the alleles DRB1*1301, DRB3*0101, and
AGDLLAIETDKATI (SEQ ID NO: 7), specific for the alleles DRB1*0701 and DRB4*0101.

Other reagents R1 may be used, in particular those described in Southwood et al. (52).

To study the HLA-DR molecules (2nd gene), this requires appropriate pairs of biotinylated peptides which should bind the preparation at low concentration and be selective for one of the two molecules. More precisely, the binding of the biotinylated peptides should be effectively inhibited by their nonbiotinylated homolog, but not greatly disrupted by the nonbiotinylated form of the other peptide (Table X). It has been possible to find such peptides for each of the molecules DRB3*0101, DRB4*0101 or DRB5*0101.

Using these tests, the peptides of Api m1 which bind these molecules were defined. The same set of peptides as above was used: peptides of 18 amino acids which cover the sequence of the allergen and peptides of 13 residues which exhaustively cover particular zones. The results obtained are illustrated in Table X below.

The DRB5*0101 allele interacts with seven different regions of Api m1. Only four and five regions of Api m1 can bind the alleles DRB4*0101 and DRB3*0101, respectively. They are mainly situated in the central and C-terminal part of the allergen. Peptides P111-123 and 122–134 indeed binds the three second molecules. It is also advantageous to note that peptides common to the 1st and 2nd DR molecules, in particular the peptides P81-93 and P85-97, exist.

TABLE X

Sensitivity and selectivity of the biotinylated peptide tracers

| | 1st DRs | | 2nd DRs | |
|---|---|---|---|---|
| Peptides | Allele | $IC_{50}$ (nM) | Allele | $IC_{50}$ (nM) |
| B1 21–36 | B1*1301 | 275 | B3*0101 | 35000 |
| LOL 191–210 | B1*1301 | >100000 | B3*0101 | 5 |
| YKL | B1*0701 | 35 | B4*0101 | 950 |
| E2/E168 | B1*0701 | 5000 | B4*0101 | 2 |
| A3 152–166 | B1*1501 | 33 | B5*0101 | 85000 |
| HA 306–318 | B1*1501 | 2500 | B5*0101 | 6.5 |

The selectivity of each peptide is evaluated by the $IC_{50}$ of the nonbiotinylated peptide tested on each of the molecules. For each pair, the first peptide is that which is selective for the 1st DR molecule and the second for the 2nd DR molecule.

The sequences of the peptides are as follows: B1 21–36 (TERVRLVTRHIYNREE) (SEQ ID NO: 5) (62), LOL 191–210 (ESWGAVWRIDTPDKLTGPFT) (SEQ ID NO: 6) (63), YKL (AAYAAAKAAALAA) (SEQ ID NO: 4) (64), HA 306–318 (PKYVKQNTLKLAT) (SEQ ID NO: 1) (65), A3 152–166 (EAEQLRAYLDGTGVE) (SEQ ID NO: 2) (65), E2/E168 (AGDLLAIETDKATI) (SEQ ID NO: 7).

Surprisingly, the method of selection according to the invention is suitable for any HLA-DR molecule.

The subject of the invention is also a kit for selecting peptides capable of desensitizing a subject allergic to bee venom, characterized in that it comprises various concentrations of fragments of 13 to 18 amino acids which overlap and which completely cover the API m1 sequence, a set of reagents R1 each consisting of a peptide fragment combined with a non-radioactive marker, such as biotin and whose sequence is different from the peptides as defined above (groups A to D) and is chosen such that it exhibits affinity toward the chosen HLA-DR molecule such that it can be used at a concentration <200 nM and an antibody specific for all the HLA-DR molecules.

Figure 3:
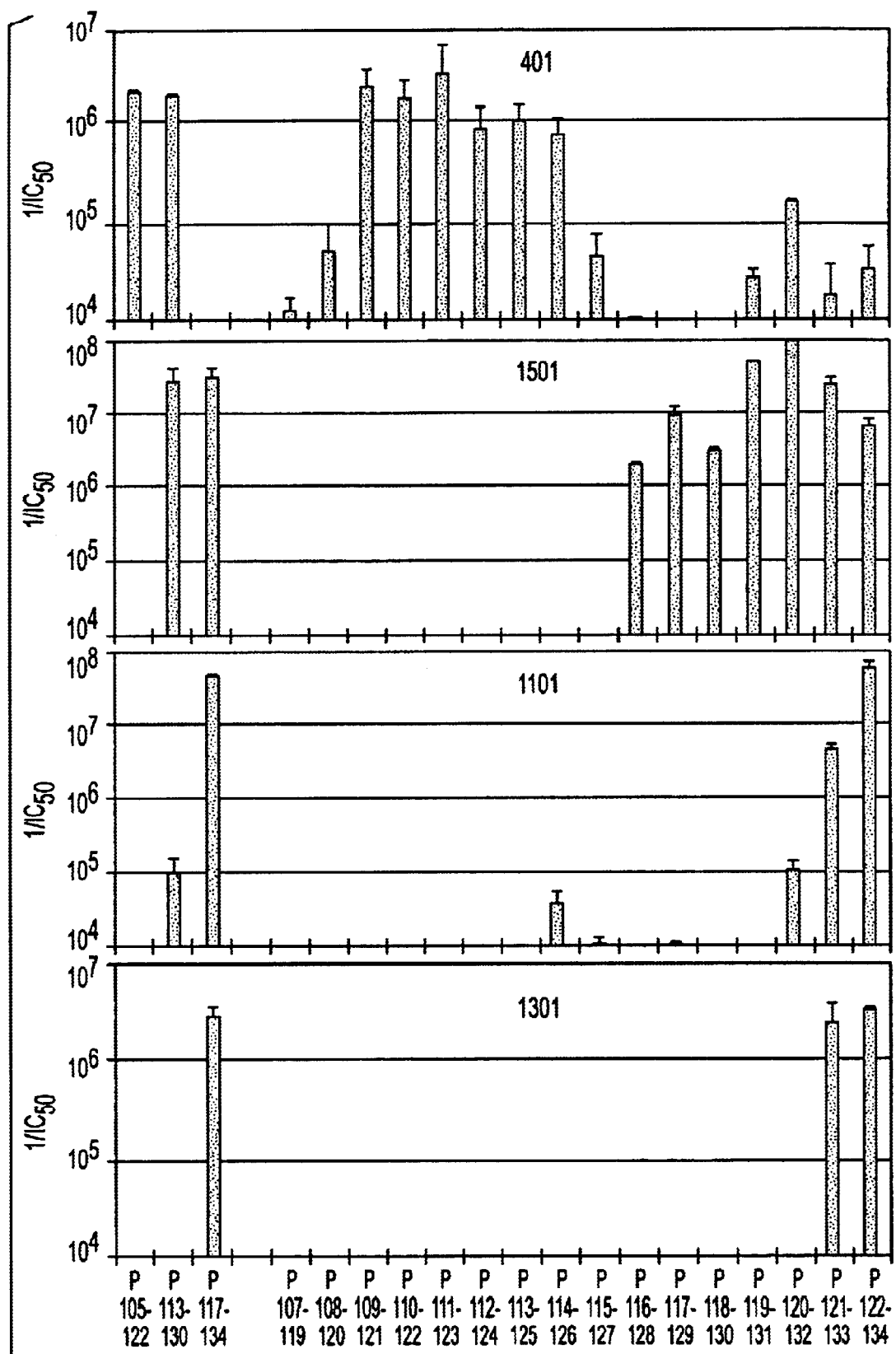
Figure 4:
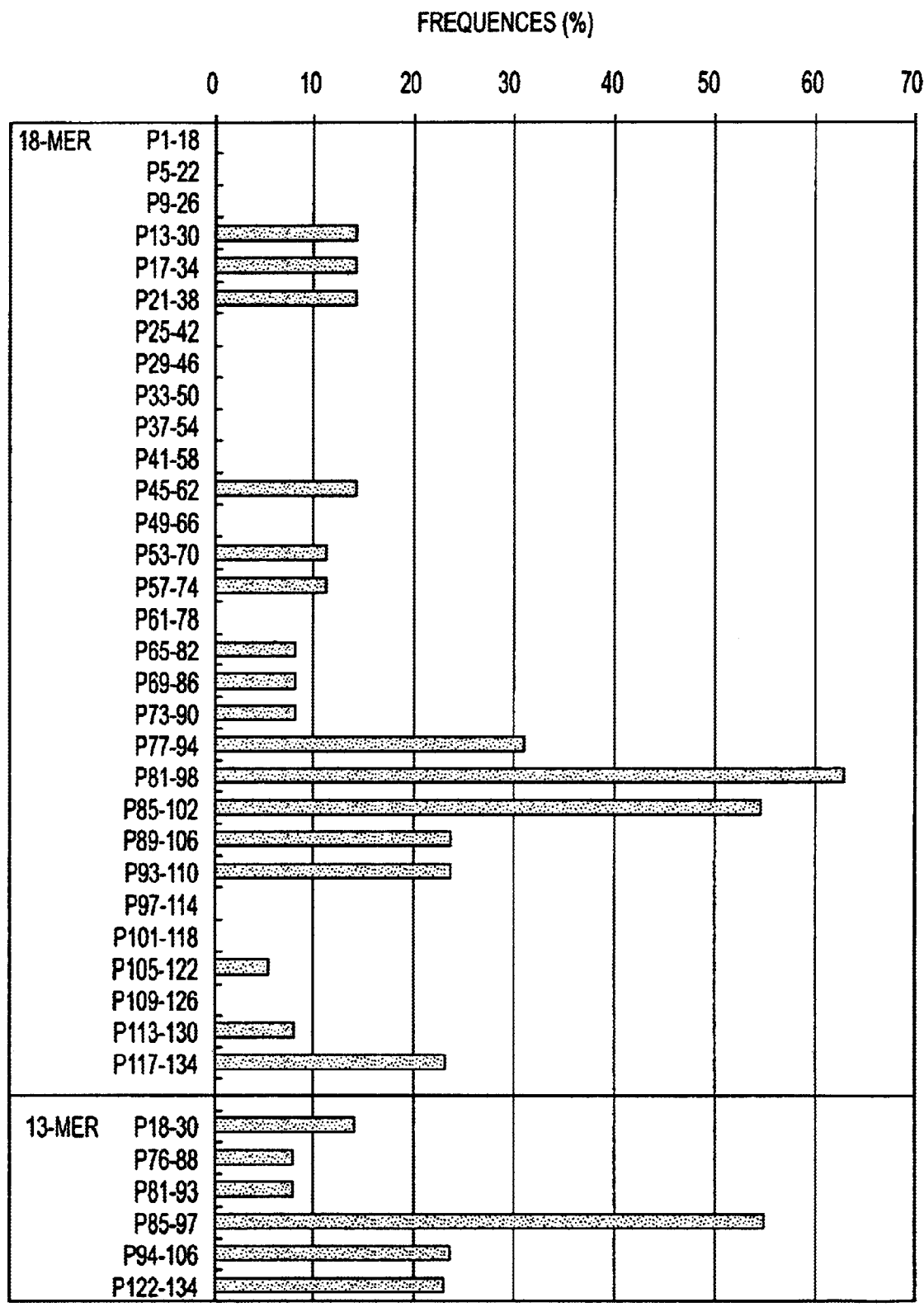
Figure 6:
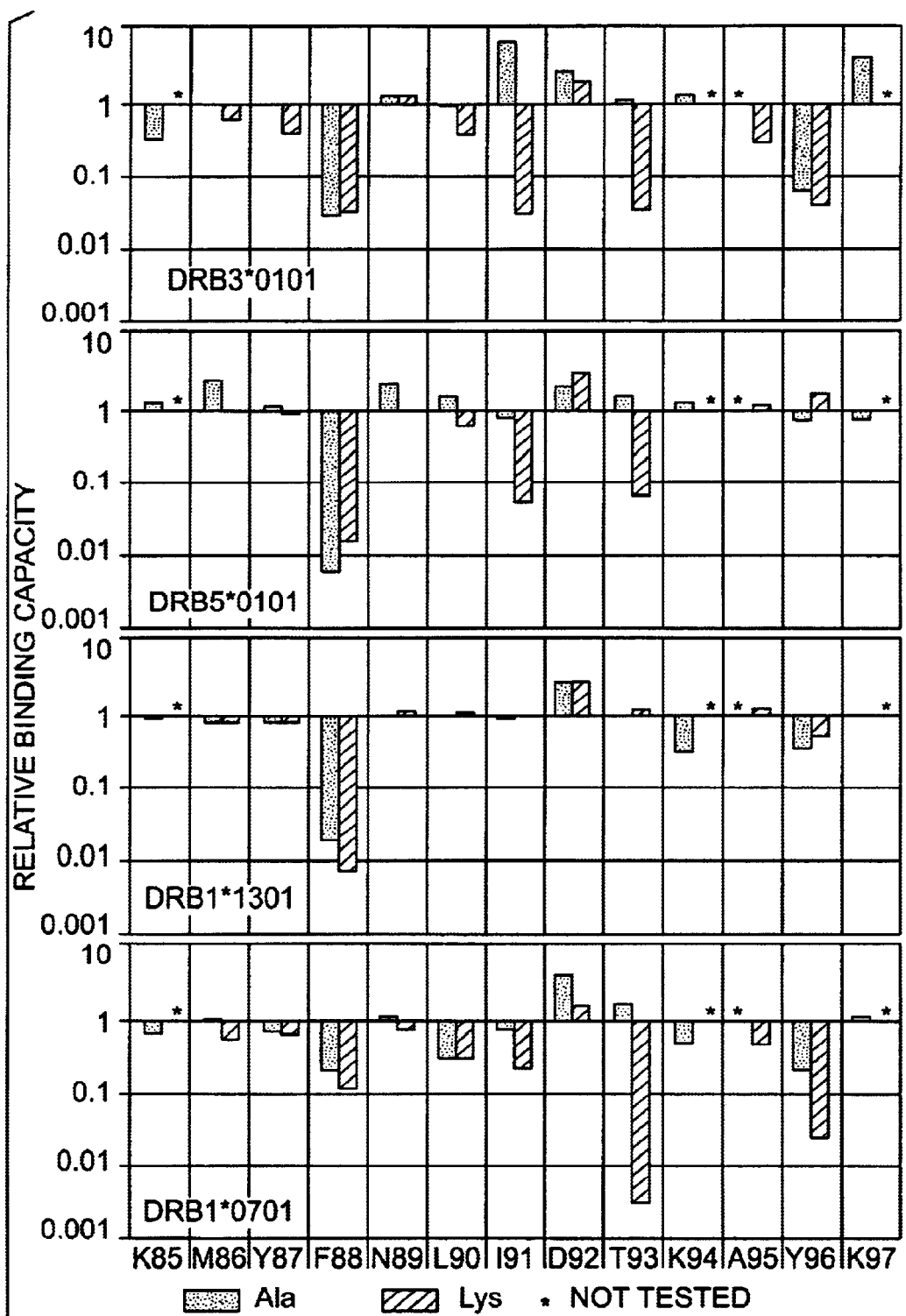
Figure 8:
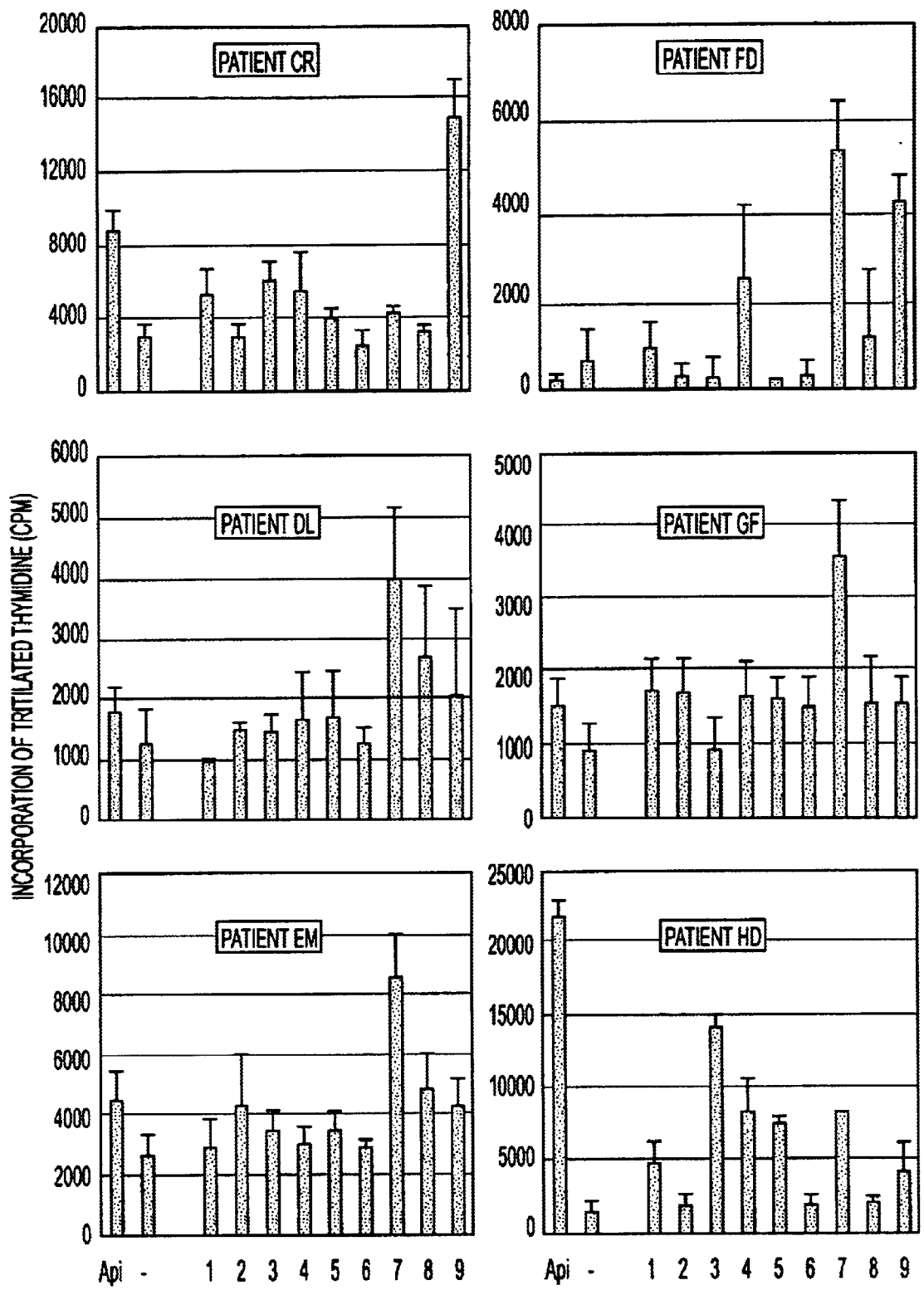

In addition to the preceding features, the invention further comprises other features which will emerge from the description which follows, which refers to exemplary embodiments of the method which is the subject of the present invention, as well as to the accompanying drawings in which:

FIG. 1 represents the protein sequence of bee venom phospholipase A2 (API m1) (SEQ ID NO: 8), deduced from that of the complementary DNA, FIG. 2 illustrates the activity for binding to the HLA-DR molecules of the peptides of thirteen amino acids which cover sequence 15–37 of the major bee venom allergen. The results are expressed in the $1/IC_{50}$ form. The unit is $M^{-1}$;

FIG. 3 illustrates the activity for binding to the HLA-DR molecules of the peptides of thirteen amino acids which cover sequence 107–134 of the major bee venom allergen. The results are expressed in the $1/IC_{50}$ form. The unit is $M^{-1}$;

FIG. 4 illustrates the frequencies of the determinants of API m1 in the Caucasian population. This representation is based on the frequencies of the alleles studied in the French population. In other Caucasian populations, substantially the same profile is found;

FIG. 5 illustrates the structure of the genes for the MHC of the HLA-DR class per haplotype; in this figure, the genes are schematically represented by black boxes and the pseudogenes by hatched blocks. The name of the genes is given above the block and that of the principal alleles present in the haplotype is given under the block;

FIG. 6 illustrates the location of the residues for anchoring the peptide P85-97 on the HLA-DR molecules. Each position was substituted by an alanine or a lysine. The results are given as relative activity with respect to the peptide P85-97A (0.01 means a relative loss by a factor of 100);

Figure 7:
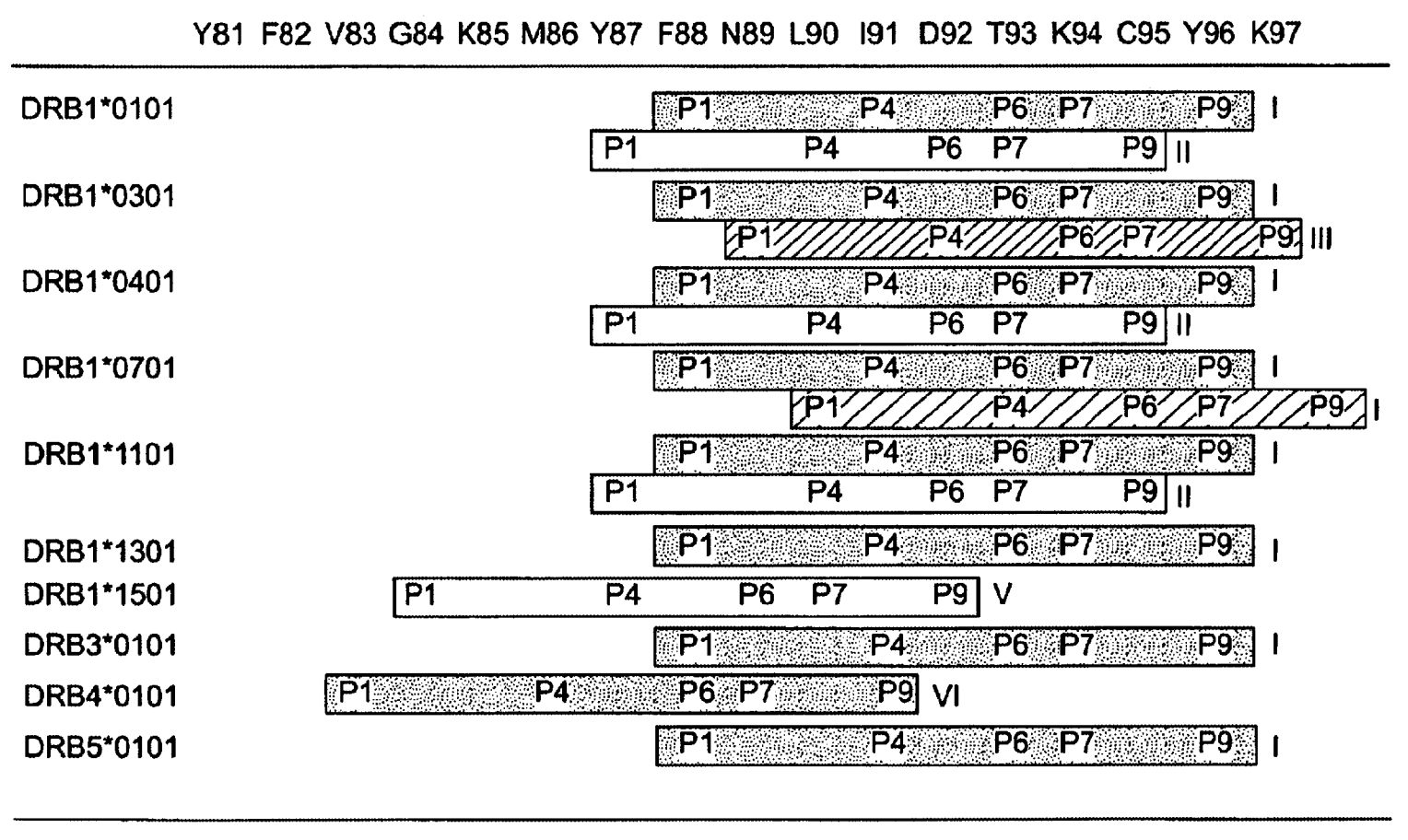

FIG. 7 illustrates the modes of binding of the sequence 81-97 to the HLA-DR molecules. The blocks schematically represent the site of binding of the HLA-DR molecules which characterize the pockets P1, P4, P6, P7 and P9. A color and a number in Roman numeral was attributed to each mode so as to facilitate their visualization; and FIG. 8 illustrates the T lymphocyte response of patients allergic to bee venom, to the peptides which cover the Api m1 sequence; the PBMCs of the allergic patients were cultured for 7 days in the presence of Api m1. At D=7 and D=10, IL2 (50 U/ml) was added. At D=14, the cells were harvested and then incubated in the presence of various peptides. The proliferation of the cells was estimated by incorporating tritiated thymidine. Composition of the pools: pool 1: P1-18, P5-22, P9-26, pool 2: P13-30, P17-34, P21-38, pool 3: P25-42, P29-46, P33-50, P37-54, pool 4: P41-58, P45-62, P49-66, pool 5: P53-70, P57-74, pool 6: P61-78, P65-82, P69-86, P73-90, pool 7: P77-94, P81-98, P85-102, P89-106, P93-110, pool 8: P97-114, P101-118, pool 9: P105-122, P109-126, P113-130, P117-134.

It should be understood, however, that these examples are given by way of illustration of the subject of the invention and do not in any manner constitute a limitation thereto.

EXAMPLE 1

Principle of the Binding Tests
Synthesis of the Peptides

The peptides which cover the sequence of the major bee venom allergen (FIG. 1) were chosen from the sequence deduced from that of the corresponding complementary DNA (36). All the peptides were synthesized according to the Fmoc strategy in solid phase parallel synthesis, purified by HPLC and checked by mass spectrometry (ES-MS).
Purification of the HLA-DR Molecules The HLA-DR molecules are purified from various homozygous EBV lines (52) by immunoaffinity. It is possible in particular to use the method described in Southwood et al. (52). Their origin and the various alleles which characterize them are described in Table IV.

TABLE IV

| Lines | Specificities | DRB1 alleles | Other DRB alleles |
|---|---|---|---|
| LG2 (52) | HLA-DR1 | DRB1*0101 | — |
| HOM2 SCHU | HLA-DR2 | DRB1*1501 | DRB5*0101 |
| MAT (52) | HLA-DR3 | DRB1*0301 | DRB3*0101 |
| STEILIN BOLETH | HLA-DR4 | DRB1*0401 | DRB4*0101 |
| PREISS (52) PITOUT (52) | HLA-DR7 | DRB1*0701 | DRB4*0101 |
| SWEIG (52) | HLA-DR11 | DRB1*1101 | DRB3*0202 |
| HHKB (46) | HLA-DR13 | DRB1*1301 | DRB3*0101 |

The hybridomas secreting a monomorphic antibody specific for the HLA-DR molecules is in particular that described in Southwood et al. (52) or that described in Posch et al. (42). The antibodies are purified from culture supernatants on Protein A-Sepharose columns. These antibodies are coupled onto Sepharose 4B or Protein A-Sepharose columns for the purification of the HLA-DR molecules.
Tests for HLA-DR/Peptide Binding The tests for binding of the peptides to the HLA-DR molecules are competition tests with immunoenzymatic visualization, initially developed by Hill on the HLA-DR molecule (37). They are carried out in 96-well plates, which makes it possible to study numerous samples in the same experiment. Briefly, the purified HLA-DR molecules are incubated with a biotinylated peptide which serves as tracer and various concentrations of the peptide to be tested.

After incubating for 24 to 72 hours, the samples are neutralized, and then 100 µl of each sample are transferred onto an ELISA plate previously sensitized by the monomorphic antibody specific for the HLA-DR molecules. The HLA-DR molecules/biotinylated peptide complexes attached at the bottom of the plate via the monomorphic antibody specific for the HLA-DR molecules are visualized by means of the streptavidin-phosphatase conjugate and a fluorescent substrate. The activity of each peptide is characterized by the concentration of this peptide which inhibits the binding of the biotinylated peptide by 50% ($IC_{50}$).
Choice and Optimization of the Binding Tests Choice of the alleles (1st gene)

The alleles studied are all the alleles in the French population whose frequency exceeds 5% of the population. They are the alleles DRB1*0101, DRB1*0301, DRB1*0401, DRB1*0701, DRB1*1101, DRB1*1301 and DRB1*1501 (Table I). They represent, on their own, 53 to 82% of the alleles in the Caucasian populations and form part of the various specificities of the HLA-DR series.

Choice of the alleles (2nd gene)

The alleles studied are the alleles most frequently encountered. They are the alleles HLA-DRB3*0101, HLA-DRB4*0101 and HLA-DRB5*0101 (see Table IIIb).

Specificity of the tests

The choice of the biotinylated peptides is the key element in the specificity of the test. Most of the cells used possess two different HLA-DR molecules which are both purified by a monomorphic antibody specific for the HLA-DR molecules and both are recognized by the same antibody. In order to unambiguously study the binding of a peptide to the DRB1 allele, it is necessary to ensure that the biotinylated peptide binds this allele and does not bind the product of the other gene.

For this purpose, a number of peptides, which are described in Table V, were used.

TABLE V

| Reagent R1 | Sequences | 1st gene (alleles DRB1) | 2nd gene (alleles DRB3, DRB4, DRB5) | References |
|---|---|---|---|---|
| HA 306–318 (=HA 307–319) | SEQ ID NO:1 | DRB1*0101 | DRB5*0101 | 37–39 |
| | | DRB1*0401 | | 37, 40, 41, 42 |
| | | DRB1*1101 | | 38, 39, 42 |
| | | DRB1*1501 | | |
| A3 152–166 | SEQ ID NO:2 | DRB1*1501 | DRB5*0101 | 43 |
| MT 2–16 | SEQ ID NO:3 | DRB1*0301 | | 44 |
| YKL | SEQ ID NO:4 | DRB1*0701 | DRB4*0101 | 41 |
| B1 21–36 | SEQ ID NO:5 | DRB1*1301 | DRB3*0101 | 46 |
| LOL 191–210 | SEQ ID NO:6 | DRB1*1301 | DRB3*0101 | 63 |
| E2/E168 | SEQ ID NO:7 | DRB1*0701 | DRB4*0101 | |

For HLA-DRB1*0101, DRB1*0401 and DRB1*1101, the peptide ha 306–318 which other authors had previously used in tests for binding to these alleles (37, 41), was used.

Likewise, for DRB1*0301 and DRB1*1501, the tracers used (reagent R1) derive from tracers which have already been described (44), (45).

For DRB1*0701, the peptide YKL has been described as being a very good ligand (41) whereas the peptide B1 21–36 is a natural ligand for DRB1*1301 (46). Neither of them has already been used as tracer.

Test conditions and sensitivity

For each HLA-DRB1 molecule, the concentration of MHC II molecules, the concentration of the biotinylated peptide, the incubation pH and the incubation time were optimized. For the molecules HLA-DRB1*101, HLA-DRB1*0401 and HLA-DRB1*0701, the conditions for the ELISA tests are similar to those already described by other authors (37, 41). For the other HLA-DRB1 molecules which were studied, there are no ELISA tests described in the literature. The details of the conditions used are described in Table VI.

TABLE VI

| Alleles | Protein concentration ($\mu$g/ml) | Tracers | Tracer concentration (nM) | Optimum pH | Incubation time (h) |
|---|---|---|---|---|---|
| DRB1*0101 | 0.6 | HA 306–318 | 10 | 6 | 24 |
| DRB1*0301 | 2.3 | MT 2–016 | 50 | 4.5 | 72 |
| DRB1*0401 | 1.6 | HA 306–318 | 30 | 6 | 24 |
| DRB1*0701 | 0.4 | YKL | 10 | 5 | 24 |
| DRB1*1101 | 1.3 | HA 306–318 | 20 | 5 | 24 |
| DRB1*1301 | 0.7 | B1 21–36 | 200 | 4.5 | 72 |
| DRB1*1501 | 0.5 | A3 152–166 | 10 | 4.5 | 24 |

The sensitivity of each test is reflected by the $IC_{50}$ values observed with the nonbiotinylated peptides which correspond to the tracers (Table VII and Table X).

TABLE VII

| Peptides | DRB1 alleles | | | | | | |
| | 101 | 401 | 1101 | 701 | 301 | 1301 | 1501 |
|---|---|---|---|---|---|---|---|
| P1–18 | 2300 | 7500 | — | 83000 | — | — | 11000 |
| P5–22 | 1900 | 10000 | — | 58000 | — | — | 22000 |
| P9–26 | — | — | — | — | — | — | 82000 |
| P13–30 | 10000 | 5000 | 8000 | 880 | — | 20000 | — |
| P17–34 | 3500 | 2000 | 13000 | 560 | 67000 | 4300 | 5500 |
| P21–38 | 1600 | 3000 | 1500 | 160 | 23000 | — | 85000 |
| P25–42 | — | — | — | 50000 | — | — | — |
| P29–46 | — | 40000 | — | 85000 | 1500 | — | — |
| P33–50 | — | 80000 | — | 78000 | 13000 | — | 90000 |
| P37–54 | — | 80000 | — | 88000 | — | — | — |
| P41–58 | — | — | — | 75000 | — | — | — |
| P45–62 | — | 68000 | — | 640 | 4300 | 1100 | 19000 |
| P49–66 | — | — | — | 1800 | 17000 | 15000 | 95000 |
| P53–70 | — | — | — | 85000 | 120 | — | — |
| P57–74 | — | 35000 | 70000 | 75000 | 40 | — | 63000 |
| P61–78 | 55000 | 29000 | 67000 | 23000 | 25000 | — | 55000 |

TABLE VII-continued

| | | | | | | | |
|---|---|---|---|---|---|---|---|
| P65–82 | 4000 | 2500 | 4000 | 2100 | 13000 | — | 730 |
| P69–86 | — | 15000 | — | 75000 | — | — | 490 |
| P73–90 | — | — | — | 75000 | — | — | 23 |
| P77–94 | 10000 | 13000 | 570 | 280 | 50000 | — | 220 |
| P81–98 | 300 | 300 | 530 | 130 | 400 | 650 | 750 |
| P85–102 | 70 | 300 | 850 | 100 | 320 | 300 | 1900 |
| P89–106 | 180 | 140 | 600 | 7600 | 50000 | — | 38000 |
| P93–110 | 350 | 220 | 750 | 72000 | 70000 | — | — |
| P97–114 | — | — | — | 77000 | 75000 | — | — |
| P101–118 | — | — | — | 30000 | — | — | — |
| P105–122 | — | 950 | 30000 | 16000 | — | — | 80000 |
| P109–126 | — | 1500 | 7000 | 12000 | 13000 | 10000 | 35000 |
| P113–130 | — | 4500 | 11000 | 6100 | 3500 | — | 79 |
| P117–134 | — | 55000 | 67 | 3700 | — | 350 | 56 |
| References | 31 | 44 | 38 | 34 | 100 | 320 | 14 |

Activity for binding to the HLA-DR molecules of the peptides of eighteen amino acids which cover the sequence of the major bee venom allergen (SEQ ID NO: 8).
-: activity ≧100000 nM The results are expressed in the form of the $IC_{50}$. The unit is nM. The $IC_{50}$ values of the best peptides ($IC_{50}$ less than 1000 nM) have been boxed.

They vary from 14 to 44 nM for the alleles 101, 401, 1101, 701 and 1501 which are very satisfactory values. They are only 100 to 320 nM for the alleles 301 and 1301, respectively, and indicate a sensitivity of average quality.

Mapping of the Determinants of API m1 Restricted to the HLA-DR Molecules Studied Localization of the determinants of API m1: by means of peptides of 18 residues The peptides which are naturally present on the HLA-DR molecules have sizes which vary between 13 and 25 amino acids approximately, the size most frequently encountered being 15 amino acids. In order to optimize the search for the peptides of API m1 which are capable of binding to the HLA-DR molecules, we synthesized thirty peptides of 18 amino acids which overlap by 14 amino acids and which therefore contain all the peptides of 15 possible residues of the API m1 sequence. The binding capacities of each of these peptides were tested on the 7 alleles which we selected and are expressed in the $IC_{50}$ form (Table VII).

Alleles 101, 401 and 1101 have a very similar activity profile and in particular accept the 4 peptides (P81-98, P85-102, P89-106 and P93-110) as ligands. However, they exhibit differences. The peptide P105-122 indeed binds the allele 401, whereas the peptides P77-94 and P117-134 bind the allele 1101. The allele 701 possesses 7 active peptides (P13-30, P17-34, P21-38, P45-62, P77-94, P81-98 and P85-102) whereas 4 peptides (P81-98, P85-102, P53-70 and P57-74) are active toward allele 301. The peptides P81-98 and P85-102 bind allele 1301 with an affinity comparable to that of the peptide P117-134. Finally, two active regions exist for allele 1501 and comprise, on the one hand, peptides P65-82, P69-86, P73-90, P77-94, P81-98 and P85-102 and, on the other hand, peptides P113-130 and P117-134.

Clearly, each allele possesses a profile for binding of the peptides of API m1 which is specific to it. Some peptides bind to only one allele (for example P105-122 to allele 401, P69-86 and P73-90 to allele 1301). Others, by contrast, bind to several alleles. That is the case in particular for peptide P81-98 which significantly binds the seven alleles studied and for peptide P85-102 which significantly binds six alleles. In many cases, a peptide is common to two or several alleles. These common peptides define mainly three distinct zones of the API m1 sequence: i) an N-terminal part which the peptides P13-30, P17-34, P21-38 form, ii) a central part consisting of the peptides P77-94 to P93-110 and iii) a C-terminal part which includes the peptides P113-122 to P117-134. It is also observed that thirteen peptides out of the thirty tested have binding activities >1000 nM, regardless of the MHC II molecule studied. They are therefore inactive or not very active.

Table VIII below illustrates the activity for binding to the HLA-DR molecules of the peptides of 13 amino acids which cover the zone 73–108 of API m1.

TABLE VIII

| Peptides | \multicolumn{7}{c}{DRB1 alleles} |
| --- | --- | --- | --- | --- | --- | --- | --- |
|  | 101 | 401 | 1101 | 701 | 301 | 1301 | 1501 |
| P73–85 |  |  |  | 28000 |  |  | 210 |
| P74–86 |  |  |  | 65000 |  |  | 330 |
| P75–87 |  |  |  | 15000 |  |  | 230 |
| P76–88 |  |  |  | 2200 |  |  | 160 |
| P77–89 |  |  | 2200 | 1400 |  |  | 780 |
| P78–90 |  | 10000 | 3000 | 1100 |  |  | 190 |
| P79–91 |  | 5000 | 3000 | 1300 |  |  | 1600 |
| P80–92 |  | — | 6000 | 2800 |  |  | 1600 |
| P81–93 |  | 2500 | 3200 | 1700 |  |  | 400 |
| P82–94 | 8000 | 530 | 4300 | — |  | — | 33000 |
| P83–95 | 4000 | 280 | 560 | 4500 | 2000 | — | — |
| P84–96 | 1900 | 2200 | 1700 | 1700 | 3700 | — | — |
| P85–97 | 120 | 210 | 570 | 63 | 600 | 58 | 33000 |
| P86–98 | 2000 | — | 1800 | 470 | 1100 | 150 | 68000 |
| P87–99 | 2500 | 22000 | 45000 | 280 | 1200 | — | 6500 |
| P88–100 | 5300 | 14000 | — | 1200 | 12000 | — | 15000 |
| P89–101 | 13000 | 13000 | — | 6000 | 45000 | — | 35000 |
| P90–102 | 3500 | 1200 | 18000 | 65000 | 60000 |  | 40000 |
| P91–103 | 870 | 380 | 3500 | 23000 |  |  | — |
| P92–104 | 270 | 120 | 7700 | — |  |  |  |
| P93–105 | 240 | 60 | 1200 | 50000 |  |  |  |
| P94–106 | 200 | 280 | 1000 | — |  |  |  |
| P95–107 | 530 | 570 | — | — |  |  |  |
| P96–108 | 1500 | 1400 | — |  |  |  |  |

Activity for binding to the HLA-DR molecules of the peptides of 13 amino acids which cover the zone 73–108 of the major bee venom allergen (SEQ ID NO: 8).
-: activity ≧100000 nM The results are expressed in the form of the $IC_{50}$. The unit is nM. The $IC_{50}$ values of the best peptides ($IC_{50}$ less than 1000 nM) have been boxed.

Precise location of the determinants of API m1

In order to better define the zones of contact between the active peptides and the MHC II molecules, all the peptides of thirteen residues which cover the active zones were synthesized. The size of the thirteen amino acids was chosen as a compromise. It corresponds to the minimum size of the peptides which are naturally present on the MHC II molecules and should be sufficiently small to discriminate between two contact surfaces contained in a single peptide of eighteen amino acids.

11 peptides which exhaustively cover the N-terminal part 15 to 37 were tested on the alleles 101, 401, 701, 1101 and 1301 (FIG. 2). For the allele 701, the peptides P18-30 to P22-34 exhibit a significant binding activity which, in the case of the peptide P18-30, is equivalent to that of the peptide of eighteen amino acids P21-38.

The alleles 401, 101 and 1101 substantially bind the same peptides as the allele 701. However, the binding activities observed are lower, which is in agreement with those obtained for the peptides of eighteen amino acids.

The central part was studied on the seven alleles by means of twenty-four peptides of thirteen residues. For the allele 101, the peptides P85-97, on the one hand, and P91-103 to P95-107, on the other hand, define two distinct zones of interaction. These two zones are also found for the alleles 401 and 1101 but with small variations. The first comprises, in addition to the peptide P85-97, the peptides P82-94 and P83-95 for the allele 401 and the peptide P83-95 for the allele 1101. The second zone of contact is strictly identical between the allele 401 and 101 whereas it is reduced to a single peptide (P94-106) for the allele 1101. The allele 701 is characterized by three peptides having good binding activity (P85-97, P86-98 and P87-99) which corresponds to that of the peptides of eighteen amino acids P81-98 and P85-102. The good activity for binding of the peptide P77-94 to the allele 701 previously described is not observed for any of the peptides of thirteen residues which cover this zone, the peptides P76-88 to P81-93 having a substantially lower activity.

The peptide P85-97 possesses, for the alleles 301 and 1301, a binding activity similar to that of the peptides of 18 amino acids P81-98 and P85-102, containing it. The allele 1301 also accepts the peptide P86-105 as ligand. For the allele 1501, seven peptides, including six which are consecutive (P73-85 to P78-90) and one which is isolated (P81-93) reflect the activity of the three peptides of eighteen amino acids (P73-90, P77-94 and P81-98)

Finally, the C-terminal part of API m1 was studied for the alleles 401, 1501, 1101 and 1301 by means of sixteen peptides of thirteen residues. The allele 401 is characterized by six active peptides (P109-121 to P114-126) whereas seven other peptides (P116-128 to P122-14) bind with a high affinity to 1501. The peptides P121-133 and 122-134 are also very active for the alleles 1101 and 1301.

These results describe the precise location of the binding determinants of the major bee venom allergen for the seven alleles chosen and clearly show the differences and the similarities between the alleles for the various peptides of API m1. In order to better account for the activity and the location of these determinants, a representative peptide, which is as short as possible and whose binding activity reflects that of the determinant (Table III) was chosen for each of them. It will be noted most particularly that the peptide P85-97 is representative of a determinant for the alleles 101, 401, 1101, 701, 301 and 1301 and that other determinants are advantageously situated near this peptide (P76-88, P77-94, P81-93, P94-106).

Frequencies of the determinants of API m1 in the Caucasian population

To evaluate the impact of the most active peptides (activity less than 1000 nM) within the Caucasian population, the cumulative frequency of the alleles which they are capable of binding (FIG. 4) was calculated for each. Applied to all the peptides of 18 amino acids which completely cover the sequence of the major allergen, this representation makes it possible to weight the activity of the peptides tested. It is clearly observed that the central zone ranging from the peptide P77-94 to the peptide P93-110 is that which has the greatest impact in the population. The peptide P81-98 binding with a good affinity to all the HLA-DRs studied, covers on its own 63% of the population and combines the impact of the determinants carried by the peptides P85-97 and P81-93. The addition of sequences at the N- and C-terminals makes it possible to add to this combination of determinants other zones of interaction such as P76-88, P77-94 and P93-106 which relate to nonnegligible percentages of the population. Finally, the impact of the peptides P117-134 or 122-134 greater than 20% is observed at the C-terminal.

EXAMPLE 2

Peptides Selected/cell Proliferation Correlation

The peptides which bind to the HLA molecules are not necessarily stimulating for the T lymphocytes. They can indeed resemble self-peptides, such that no T lymphocyte will be capable of recognizing them. On the other hand, it has previously been shown that all the peptides which stimulate the T lymphocytes are part of the best peptides which bind to the MHC II molecules (60). The binding to the MHC II molecules is therefore a necessary but insufficient condition for allowing a peptide to be recognized by the T lymphocytes. In order to verify that the peptides which were identified are effectively capable of stimulating T lymphocytes in allergic patients, their stimulating capacity was tested (FIG. 8). The cells used are peripheral blood cells from people allergic to bee venom. These people came to the Rothschild Hospital to be desensitized and agreed to participate in this study (DGS No. 980457). Given the small number of cells, the peptides were grouped into different pools. The cells from one patient did not result in any proliferation (not shown). Of the six patients for whom reactivity was observed, a high variability was observed in the intensity of the response to the peptides, in the nature and the number of active peptides. However, it is observed that of the 6 patients, 5 respond to pool 7 which comprises peptides which cover zone 77–111 and 3 respond to pool 9 which covers zone 105–134.

The other peptides can respond strongly but in a manner specific to a given patient (example: pool 3 with the patient HD). Consequently, these results confirm the benefit of the use of the sequence 76–106 for desensitization and, to a lesser degree, of the C-terminal region: 105–134.

REFERENCES

1. MULLER U. R. et al., *Monogr. Allergy*, 1993, 31, 131.
2. MULLER U. R. et al., *Clin. Exp. Allergy*, 1998, 28, 4.
3. MULLER U. et al., *J. Allergy Clin. Immunol.*, 1992, 89, 529.
4. KING T. P. et al., *Arch. Biochem. Biophys.*, 1976, 172, 661.
5. V. LIEBERS et al., *Clin. Exp. Allergy*, 1996, 26, 494.
6. CHRETIEN I. et al., *Eur. J. Immunol.*, 1990, 20, 243.
7. HUSSAIN R. et al., *J. Immunol.*, 1992, 148, 2731.
8. ROCKLIN R. E. et al., *N. Engl. J. Med.*, 1980, 302, 1213.
9. AKDIS C. A. et al., *J. Clin. Invest.*, 1996, 98, 1676.
10. KAMMERER R. et al., *J. Allergy Clin. Immunol.*, 1997, 100, 96.
11. JUTEL M. et al., *J. Immunol.*, 1995, 154, 4187.
12. SECRIST H. et al., *J. Exp. Med.*, 1993, 178, 2123.
13. MILICH D. R. et al., *J. Immunol.*, 1989, 143, 3148.
14. BURSTEIN H. J. et al., *J. Immunol.*, 1992, 148, 3687.
15. GERMAIN R. N. et al., *Annu. Rev. Immunol.*, 1993, 11, 403.
16. BRINER T. J. et al., *Proc. Natl. Acad. Sci. USA*, 1993, 90, 7608.
17. HOYNE G. F. et al., *J. Exp. Med.*, 1993, 178, 1783.
18. BAUER L. et al., *Clin. Exp. Immunol.*, 1997, 107, 536.
19. VRTALA S. et al., *Int. Arch. Allergy Immunol.*, 1997, 113, 246.
20. PESCE A. J. et al., *Int. Arch. Allergy Appl. Immunol.*, 1990, 92, 88.
21. LITWIN A. et al., *Int. Arch. Allergy Appl. Immunol.*, 1988, 87, 361.
22. MULLER U., *J. Allergy Clin. Immunol.*, 1998, 101, 747.
23. DHILLON M., *J. Allergy Clin. Immunol.*, 1992, 90, 42.
24. CARBALLIDO J. M., *J. Immunol.*, 1993, 150, 3582.
25. DUDLER T. et al., *Eur. J. Immunol.*, 1995, 25, 538.
26. NORMAN P. S. et al., *Am. J. Respir. Crit. Care Med.*, 1996, 154, 1623.
27. TAKAI T. et al., *Nat. Biotechnol.*, 1997, 15, 754.
28. SMITH A. M. et al., *J. Allergy Clin. Immunol.*, 1998, 101, 423.
29. FERREIRA F. et al., *Faseb J.*, 1998, 12, 231.
30. KAMMERER R. et al., *Clin. Exp. Allergy*, 1997, 27, 1016.
31. VAN NEERVEN R. J. et al., *Immunol. Today*, 1996, 17, 526.
32. FAUX J. A. et al., *Clin. Exp. Allergy*, 1997, 27, 578.
33. LYMPANY P. et al., *J. Allergy Clin. Immunol.*, 1990, 86, 160.
34. LUCAS A. et al., *Immunogenetics*, 1986, 23, 417.
35. COLOMBANI J., 1993, John Libbey Eurotext, *HLA: fonctions immunitaires et applications médicales* [immune functions and medical applications].
36. KUCHLER K. et al., *Eur. J. Biochem.*, 1989, 184, 249.
37. HILL C. M. et al., *J. Immunol.*, 1994, 152, 2890.
38. ROCHE P. A. et al., *J. Immunol.*, 1990, 144, 1849.
39. O'SULLIVAN D. et al., *J. Immunol.*, 1990, 145, 1799.
40. SETTE A. et al., *J. Immunol.*, 1993, 151, 3163.
41. MARSHALL K. W. et al., *J. Immunol.*, 1994, 152, 4946.
42. POSCH P. E. et al., *Eur. J. Immunol.*, 1996, 26, 1884.
43. VOGT A. B. et al., *J. Immunol.*, 1994, 153, 1665.
44. GELUK A. et al., *J. Immunol.*, 1992, 149, 2864.
45. SIDNEY J. et al., *J. Immunol.*, 1992, 149, 2634.
46. DAVENPORT M. P. et al., *Proc. Natl. Acad. Sci. USA*, 1995, 92, 6567.
47. HAMMER J. et al., *Adv. Immunol.*, 1997, 66, 67.

48. SHIPOLINI R. A. et al., *Eur. J. Biochem.,* 1974, 48, 465.
49. MAILLERE B. et al., *Mol. Immunol.,* 1995, 32, 1073.
50. MAILLERE B. et al., *Mol. Immunol.,* 1995, 32, 1377.
51. COTTON J. et al., *Int. Immunol.,* 1998, 10, 159.
52. SOUTHWOOD S. et al., *J. Immunol.,* 1998, 160, 3363–3373.
53. NICOLAS J. P. et al., *J. Biol. Chem.,* 1997, 272, 11, 7173–7181.
54. GHOMASHCHI F. et al., *Biochem.,* 1998, 37, 6697–6710.
55. DUDLER T. et al., *J. Immunol.,* 1994, 152, 5514–5522.
56. IRLE C. et al., *J. Exp. Med.,* 1988, 167, 853.
57. FRIEDL-HAJEK R. et al., *Clin. Exp. Allergy,* 1999, 29, 478.
58. KIM J. et al., *J. Immunol.,* 1997, 159, 335.
59. SHIMODA S. et al., *J. Exp. Med.,* 1995, 181, 1835.
60. TEXIER C. et al., *Int. Immunol.,* 1999, 11.
61. RAMMENSEE H. G. et al., *Immunogenetics,* 1995, 41, 178.
62. DAVENPORT M. P. et al., *Proc. Natl. Acad. Sci. USA,* 1995, 92, 6567.
63. SIDNEY J. C. et al., *J. Immunol.,* 1992, 149, 2634.
64. MARSHALL K. W. et al., *J. Immunol.,* 1994, 152, 4946.
65. VOGT A. B. et al., *Immunol.,* 1994, 153, 1665.

As is evident from the above, the invention is not at all limited to those of its embodiments, implementations and applications which have just been described more explicitly; it encompasses, on the contrary, all the variants which may occur to the specialist in this field, without departing from the framework or the scope of the present invention.

What is claimed:

1. A polypeptide molecule capable of desensitizing a human subject to bee venom, the polypeptide selected from the group consisting of: (a) a polypeptide molecule corresponding to amino acid positions 85–97 of SEQ ID NO: 8; (b) a polypeptide molecule corresponding to amino acid positions 81–93 of SEQ ID NO: 8; (c) a polypeptide molecule corresponding to amino acid positions 94–106 of SEQ ID NO: 8; (d) a polypeptide molecule corresponding to amino acid positions 76–88 of SEQ ID NO: 8; (e) a polypeptide molecule corresponding to amino acid positions 77–94 of SEQ ID NO: 8; (f) a polypeptide molecule corresponding to amino acid positions 122–134 of SEQ ID NO: 8; and (g) a polypeptide molecule of (a)–(f) comprising at least one amino acid substitution, wherein the substituted polypeptide exhibits binding activity to MHC class II molecules identical to or greater than that of the polypeptides (a)–(f).

2. A polypeptide molecule of claim 1, wherein said at one amino acid sustitution occurs at a position corresponding to amino acid position 83, 84 or 86 to 97 of SEQ ID NO: 8.

3. A polypeptide molecule of claim 2, wherein the at least one amino acid sustitution is selected from the group consisting of N89L, N89T, C95A, G84L and G84I.

4. A polymer molecule comprising at least one polypeptide of claim 1.

5. A pharmaceutical composition for desensitizing a human subject to bee venom, the composition comprising:
 at least one polypeptide molecule corresponding to amino acid positions 85–97 of SEQ ID NO: 8 or to amino acid positions 81–93 of SEQ ID NO: 8;
 at least one polypeptide molecule of at least 13 amino acids and corresponding to a consecutive amino acid sequence within the range of amino acid positions 81–97 of SEQ ID NO: 8 and which binds to at least one HLA-DR molecule encoded by the HLA alleles DRB1*0101, DRB1*0301, DRB1*0401, DRB1*0701, DRB1*1101, DRB1*1301 or DRB1*1501 with a binding activity <1000 nM; and
 at least one pharmaceutically acceptable vehicle.

6. A pharmaceutical composition for desensitizing a human subject to bee venom comprising:
 (a) at least one polypeptide molecule corresponding to amino acid positions 85–97 of SEQ ID NO: 8 or to amino acid positions 81–93 of SEQ ID NO: 8;
 (b) at least one polypeptide molecule of at least 13 amino acids and corresponding to a consecutive amino acid sequence within the range of amino acid positions 81–97 of SEQ ID NO: 8 and which binds to at least one HLA-DR molecule encoded by the HLA alleles DRB1*0101, DRB1*0301, DRB1*0401, DRB1*0701, DRB1*1101, DRB1*1301 or DRB1*1501 with a binding activity <1000 nM;
 (c) at least one polypeptide molecule corresponding to amino acid positions 94–106 of SEQ ID NO: 8 or a polymer thereof;
 (d) at least one polypeptide molecule of at least 13 amino acids and corresponding to a consecutive amino acid sequence within the range of amino acid positions 94–106 of SEQ ID NO: 8, the molecule binding to at least one HLA-DR molecule encoded by the alleles DRB1*0101, DRB1*0401 or DRB1*1101 with a binding activity <1000 nM;
 (e) at least one polypeptide molecule corresponding to amino acid positions 76–88 or 77–94 of SEQ ID NO: 8 or a polymer thereof;
 (f) at least one polypeptide molecule of at least 13 amino acids and corresponding to a consecutive amino acid sequence within the range of amino acid positions 76–94 of SEQ ID NO: 8, the molecule binding to at least one HLA-DR molecule encoded by the alleles DRB1*0701, DRB1*1101 or DRB1*1501 with a binding activity <1000 nM;
 (g) at least one polypeptide molecule corresponding to amino acid positions 122–134 of SEQ ID NO: 8 or a polymer thereof;
 (h) at least one polypeptide molecule of at least 13 amino acids and corresponding to a consecutive amino acid sequence within the range of amino acid positions 122–134 of SEQ ID NO: 8, the molecule binding to at least one HLA-DR molecule encoded by the alleles DRB1*1101, DRB1*1301 or DRB1*1501 with a binding activity <1000 nM; and
 (i) at least one pharmaceutically acceptable vehicle,
 wherein any polypeptide may contain at least one mutation such that the resultant mutant binds at least to one HLA-DR molecule encoded by the alleles DRB1*0101, DRB1*0301, DRB1*0401, DRB1*0701, DRB1*1101, DRB1*1301 or DRB1*1501 with a binding activity <1000 nM.

7. A pharmaceutical composition of claim 6, further comprising at least one polypeptide molecule selected from the group consisting of a polypeptide molecule corresponding to amino acid positions 18–30 of SEQ ID NO: 8, a polypeptide molecule corresponding to amino acid positions 45–62 of SEQ ID NO: 8, a polypeptide molecule corresponding to amino acid positions 57–74 of SEQ ID NO: 8, a polypeptide molecule corresponding to amino acid positions 65–82 of SEQ ID NO: 8, a polypeptide molecule corresponding to amino acid positions 111–123 of SEQ ID NO: 8, a polypeptide molecule corresponding to amino acid positions 21–38 of SEQ ID NO: 8, a polypeptide molecule corresponding to amino acid positions 53–70 of SEQ ID NO: 8 and a polypeptide molecule corresponding to amino acid positions 89–101 of SEQ ID NO: 8.

8. A pharmaceutical composition of claim 6, further comprising a polypeptide molecule selected from the group consisting of a polypeptide molecule corresponding to amino acid positions 81–97 of SEQ ID NO: 8, a polypeptide molecule corresponding to amino acid positions 76–94 of SEQ ID NO: 8 and a polypeptide molecule corresponding to amino acid positions 76–106 of SEQ ID NO: 8.

9. A pharmaceutical composition for desensitizing a human subject to bee venom, the composition comprising:
 a polypeptide molecule selected from the group consisting of a polypeptide molecule corresponding to amino acid positions 81–97 of SEQ ID NO: 8, a polypeptide molecule corresponding to amino acid positions 76–94 of SEQ ID NO: 8 and a polypeptide molecule corresponding to amino acid positions 76–106 of SEQ ID NO: 8; and
 at least one pharmaceutically acceptable vehicle.

10. A pharmaceutical composition for desensitizing a human subject to bee venom, the composition comprising:
 a polypeptide molecule according to SEQ ID NO: 8, wherein the molecule has at least one mutation at an amino acid position within the range of amino acid positions 1–17, 39–44 or 107–110, wherein the mutated molecule no longer exhibits reactivity toward IgE molecules; and
 at least one pharmaceutically acceptable vehicle.

11. A method of desensitizing a human subject to bee venom, comprising administering to the subject a therapeutically effective amount of a pharmaceutical composition of any one of claims 5, 6, 9, or 10, wherein, after effective administration of said compound, the subject is desensitized to bee venom.

12. A method of desensitizing a human subject to bee venom, comprising administering to the subject a therapeutically effective amount of a pharmaceutical composition of claim 7, wherein, after effective administration of said compound, the subject is desensitized to bee venom.

13. A method of desensitizing a human subject to bee venom, comprising administering to the subject a therapeutically effective amount of a pharmaceutical composition of claim 8, wherein, after effective administration of said compound, the subject is desensitized to bee venom.

* * * * *

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: Fragment binding HLA-DR alleles

<400> SEQUENCE: 1

Pro Lys Tyr Val Lys Gln Asn Thr Leu Lys Leu Ala Thr
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Fragment binding HLA-DR alleles

<400> SEQUENCE: 2

Glu Ala Glu Gln Leu Arg Ala Tyr Leu Asp Gly Thr Gly Val Glu
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Fragment binding HLA-DR alleles

<400> SEQUENCE: 3

Ala Lys Thr Ile Ala Tyr Asp Glu Glu Ala Arg Gly Leu Glu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Fragment binding HLA-DR alleles

<400> SEQUENCE: 4

Ala Ala Tyr Ala Ala Ala Lys Ala Ala Ala Leu Ala Ala
1               5                   10

<210> SEQ ID NO 5
```

```
<211> LENGTH: 16
<212> TYPE: PRT
<213> ORGANISM: Artificial Sequence
<220> FEATURE:
<223> OTHER INFORMATION: Fragment binding HLA-DR alleles

<400> SEQUENCE: 5

Thr Glu Arg Val Arg Leu Val Thr Arg His Ile Tyr Asn Arg Glu Glu
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Fragment binding HLA-DR alleles

<400> SEQUENCE: 6

Glu Ser Trp Gly Ala Val Trp Arg Ile Asp Thr Pro Asp Lys Leu Thr
1               5                   10                  15

Gly Pro Phe Thr
            20

<210> SEQ ID NO 7
<211> LENGTH: 14
<212> TYPE: PRT
<213> ORGANISM: Artificial Sequence
<220> FEATURE:
<223> OTHER INFORMATION: Fragment binding HLA-DR alleles

<400> SEQUENCE: 7

Ala Gly Asp Leu Leu Ala Ile Glu Thr Asp Lys Ala Thr Ile
1               5                   10

<210> SEQ ID NO 8
<211> LENGTH: 134
<212> TYPE: PRT
<213> ORGANISM: Apis mellifera

<400> SEQUENCE: 8

Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
                20                  25                  30

Thr His Asp Met Cys Pro Asp Val Met Ser Ala Gly Glu Ser Lys His
            35                  40                  45

Gly Leu Thr Asn Thr Ala Ser His Thr Arg Leu Ser Cys Asp Cys Asp
        50                  55                  60

Asp Lys Phe Tyr Asp Cys Leu Lys Asn Ser Ala Asp Thr Ile Ser Ser
65                  70                  75                  80

Tyr Phe Val Gly Lys Met Tyr Phe Asn Leu Ile Asp Thr Lys Cys Tyr
                85                  90                  95

Lys Leu Glu His Pro Val Thr Gly Cys Gly Glu Arg Thr Glu Gly Arg
            100                 105                 110

Cys Leu His Tyr Thr Val Asp Lys Ser Lys Pro Lys Val Tyr Gln Trp
        115                 120                 125

Phe Asp Leu Arg Lys Tyr
    130
```